US009482512B2

(12) United States Patent
Hess

(10) Patent No.: US 9,482,512 B2
(45) Date of Patent: Nov. 1, 2016

(54) METHODS FOR 3-DIMENSIONAL INTERFEROMETRIC MICROSCOPY

(71) Applicant: Howard Hughes Medical Institute, Chevy Chase, MD (US)

(72) Inventor: Harald F. Hess, Leesburg, VA (US)

(73) Assignee: Howard Hughes Medical Institute, Chevy Chase, MD (US)

( * ) Notice: Subject to any disclaimer, the term of this patent is extended or adjusted under 35 U.S.C. 154(b) by 0 days.

(21) Appl. No.: 14/820,676

(22) Filed: Aug. 7, 2015

(65) Prior Publication Data

US 2016/0054112 A1 Feb. 25, 2016

Related U.S. Application Data

(60) Division of application No. 14/302,153, filed on Jun. 11, 2014, now Pat. No. 9,127,925, which is a continuation of application No. 13/051,670, filed on Mar. 18, 2011, now Pat. No. 8,780,442, which is a (Continued)

(51) Int. Cl.
*G02B 21/00* (2006.01)
*G01B 9/02* (2006.01)
(Continued)

(52) U.S. Cl.
CPC ....... *G01B 9/02041* (2013.01); *G01B 9/02007* (2013.01); *G01B 9/02081* (2013.01); *G01B 9/02097* (2013.01); *G01B 9/04* (2013.01); *G01N 21/6456* (2013.01); *G01N 21/6458* (2013.01);
(Continued)

(58) Field of Classification Search
CPC ............. G02B 21/14; G02B 21/0056; G02B 21/0032; G02B 21/06; G02B 21/16
USPC ........ 359/362–373, 618–638, 388, 434–435, 359/577–590, 362–373; 356/450–521, 356/364–365
See application file for complete search history.

(56) References Cited

U.S. PATENT DOCUMENTS 4,944,590 A 7/1990 Poisel et al.
5,392,116 A 2/1995 Makosch
(Continued)

FOREIGN PATENT DOCUMENTS

JP 01-272905 10/1989
JP 2001-133215 A 5/2001
(Continued)

OTHER PUBLICATIONS

Betzig et al., Supporting online material for "Imaging Intracellular Fluorescent Proteins at Nanometer Resolution", Science Express, Aug. 10, 2006, pp. 1-30.
(Continued)

*Primary Examiner* — Bumsuk Won
*Assistant Examiner* — Tamara Y Washington
(74) *Attorney, Agent, or Firm* — DiBerardino McGovern IP Group LLC

(57) ABSTRACT

A method includes sequentially acquiring phase-shifted images of an optical source in a plurality of predetermined positions in the z plane to form a plurality of image frame sequences; determining from the plurality of image frame sequences at least one phase-related characteristic associated with each predetermined position of the optical source in the z plane; and storing the at least one phase-related characteristic and the predetermined positions of the optical source in the z plane.

22 Claims, 28 Drawing Sheets

Related U.S. Application Data division of application No. 11/961,601, filed on Dec. 20, 2007, now Pat. No. 7,916,304.

(60) Provisional application No. 60/871,366, filed on Dec. 21, 2006, provisional application No. 60/908,307, filed on Mar. 27, 2007.

(51) Int. Cl.

| | | |
|---|---|---|
| *G01B 9/04* | (2006.01) | |
| *G01N 21/64* | (2006.01) | |
| *G02B 21/36* | (2006.01) | |
| *H04N 13/02* | (2006.01) | |
| *G02B 21/14* | (2006.01) | |

(52) U.S. Cl.
CPC ......... *G02B 21/008* (2013.01); *G02B 21/0056* (2013.01); *G02B 21/0076* (2013.01); *G02B 21/14* (2013.01); *G02B 21/367* (2013.01); *H04N 13/0214* (2013.01); *G01B 2290/45* (2013.01); *G01B 2290/55* (2013.01)

(56) References Cited

U.S. PATENT DOCUMENTS

| | | |
|---|---|---|
| 5,671,085 A | 9/1997 | Gustafsson et al. |
| 6,139,166 A | 10/2000 | Marshall et al. |
| 6,304,330 B1 | 10/2001 | Millerd et al. |
| 6,388,788 B1 | 5/2002 | Harris et al. |
| 6,537,829 B1 | 3/2003 | Zarling et al. |
| 6,570,705 B2 | 5/2003 | Bewersdorf et al. |
| RE38,307 E | 11/2003 | Gustafsson et al. |
| 6,687,008 B1 | 2/2004 | Peale et al. |
| 6,891,670 B2 | 5/2005 | Gugel et al. |
| 7,064,824 B2 | 6/2006 | Hell |
| 7,253,893 B2 | 8/2007 | Hell et al. |
| 7,274,506 B2 | 9/2007 | Engelhardt |
| 7,333,690 B1 | 2/2008 | Peale et al. |
| 7,463,344 B2 | 12/2008 | Wolleschensky et al. |
| 7,573,577 B2 | 8/2009 | Martinez |
| 2001/0012151 A1 | 8/2001 | Knebel et al. |
| 2002/0098516 A1 | 7/2002 | Cosgrove |
| 2002/0105722 A1 | 8/2002 | Bewersdorf et al. |
| 2003/0016364 A1* | 1/2003 | Thomas ................ G01B 9/021 356/457 |
| 2003/0092884 A1 | 5/2003 | Lukyanov et al. |
| 2004/0004723 A1 | 1/2004 | Seko et al. |
| 2004/0080750 A1 | 4/2004 | Wolf et al. |
| 2006/0038993 A1 | 2/2006 | Hell |
| 2006/0119861 A1 | 6/2006 | Saunders et al. |
| 2006/0256343 A1 | 11/2006 | Choma et al. |

FOREIGN PATENT DOCUMENTS

| | | |
|---|---|---|
| JP | 2002-013911 | 1/2002 |
| JP | 2002-221668 A | 8/2002 |
| WO | 01/96372 A2 | 12/2001 |
| WO | 01/96373 A2 | 12/2001 |
| WO | 2004/109286 A2 | 12/2004 |
| WO | 2006/058187 A2 | 6/2006 |
| WO | 2006/123967 A2 | 11/2006 |
| WO | 2006/127692 A2 | 11/2006 |

OTHER PUBLICATIONS

Tsutsui et al., "Semi-Rational Engineering of a Coral Fluorescent Protein into an Efficient Highlighter.", EMBO reports, vol. 6, No. 3, Mar. 2005, pp. 233-238.
Betzig, E., "Proposed Method for Molecular Optical Imaging", Optics Letters, vol. 20, No. 3, Feb. 1, 1995, pp. 237-239.
Oijen et al., "Far-Field Fluorescence Microscopy beyond the Diffraction Limit", Journal of the Optical Society of America A., vol. 16, No. 4, 1999, pp. 909-915.
Cheezum et al.,"Quantitative Comparison of Algorithms for Tracking Single Fluorescent Particles", Biophysical Journal, vol. 81, No. 4, Oct. 2001, pp. 2378-2388.
Chudakov et al.,"Photoswitchable Cyan Fluorescent Protein for Protein Tracking", Nature Biotechnology, vol. 22, No. 11, Nov. 2004, pp. 1435-1439.
Cole et al., "Diffusional Mobility of Golgi Proteins in Membranes of Living Cells", Science, vol. 273, No. 5276, Aug. 9, 1996, pp. 797-801.
Eisenstein, Michael, "New Fluorescent Protein Includes Handy On-Off Switch", Nature Methods, vol. 2, No. 1, Jan. 2005, pp. 8-9.
Wiedenmann et al., "EosFP, A Fluorescent Marker Protein with UV-Inducible Green-To-Red Fluorescence Conversion", PNAS, vol. 101, No. 45, Nov. 9, 2004, pp. 15905-15910.
Betzig et al., "Single Molecules Observed by Near-Field Scanning Optical Microscopy", Science, vol. 262, No. 5, Nov. 26, 1993, pp. 1422-1425.
Gustafsson, M. G. L., "Surpassing the Lateral Resolution Limit by a Factor of Two Using Structured Illumination Microscopy", Journal of Microscopy, vol. 198, Pt 2, May 2000, pp. 82-87.
Lidke et al., "Superresolution by Localization of Quantum Dots Using Blinking Statistics", Optics Express, vol. 13, No. 18, Sep. 5, 2005, pp. 7052-7062.
Hess et al., "Near-Field Spectroscopy of the Quantum Constituents of a Luminescent System", Science, vol. 264, No. 5166, Jun. 17, 1994, pp. 1740-1745.
Hofmann et al.,"Breaking the Diffraction Barrier in Fluorescence Microscopy at Low Light Intensities by Using Reversibly Photoswitchable Proteins", PNAS, vol. 102, No. 49, Dec. 6, 2005, pp. 17565-17569.
Chudakov et al., "Kindling Fluorescent Proteins for Precise in Vivo Photolabeling", Nature Biotechnology, vol. 21, No. 2, Feb. 2003, pp. 191-194.
Schwartz et al., "Development and Use of Fluorescent Protein Markers in Living Cells", Science, vol. 300, No. 5616, Apr. 4, 2003, pp. 87-91.
Lukyanov et al., "Photoactivatable Fluorescent Proteins", Nat. Rev. Molec. Cell Bio., vol. 6, Nov. 2005, pp. 885-891.
Ando et al., "Regulated Fast Nucleocytoplasmic Shuttling Observed by Reversible Protein Highlighting", Science, vol. 306, No. 5700, Nov. 19, 2004, pp. 1370-1373.
Moerner, W E., "High-Resolution Optical Spectroscopy of Single Molecules in Solids", Acc. Chem. Res., vol. 29, No. 12, Dec. 1996, pp. 563-571.
Qu et al., "Nanometer-Localized Multiple Single-Molecule Fluorescence Microscopy", PNAS., vol. 101, No. 31, Aug. 3, 2004, pp. 11298-11303.
Patterson et al., "A Photoactivatable GFP for Selective Photolabeling of Proteins and Cells", Science, vol. 297, No. 5588, Sep. 13, 2002, pp. 1873-1877.
Politz, Joan C., "Use of Caged Fluorochromes to Track Macromolecular Movement in Living Cells", Trends in Cell Biology, vol. 9, No. 7, Jul. 1999, pp. 284-287.
Hermida-Matsumoto et al., "Localization of Human Immunodeficiency Virus Type 1 Gag and Env at the Plasma Membrane by Confocal Imaging", Journal of Virology, vol. 74, No. 18, Sep. 2000, pp. 8670-8679.
Gordon et al., "Single-Molecule High-Resolution Imaging with Photobleaching", PNAS, vol. 101, No. 17, Apr. 27, 2004, pp. 6462-6465.
Churchman et al., "Single Molecule High-Resolution Colocalization of Cy3 and Cy5 Attached to Macromolecules Measures Intramolecular Distances Through Time", PNAS, vol. 102, Feb. 1, 2005, pp. 1419-1423.
Westphal et al., "Nanoscale Resolution in the Focal Plane of an Optical Microscope", PRL, vol. 94, No. 14, Apr. 15, 2005, pp. 143903-1 to 143903-4.
Frohn et al., "True Optical Resolution Beyond the Rayleigh Limit Achieved by Standing Wave Illumination", PNAS, vol. 97, No. 13, Jun. 20, 2000, pp. 7232-7236.
Thompson et al., "Precise Nanometer Localization Analysis for Individual Fluorescent Probes", Biophysical Journal, vol. 82, No. 5, May 2002, pp. 2775-2783.

(56) References Cited

OTHER PUBLICATIONS

Chen et al., "Site-Specific Labeling of Proteins with Small Molecules in Live Cells", Current Opinion in Biotechnology, vol. 16, No. 1, Feb. 2005, pp. 35-40.
Yildiz et al., "Myosin V Walks Hand-Over-Hand: Single Fluorophore Imaging with 1.5-nm Localization", Science, vol. 300, No. 5628, Jun. 27, 2003, pp. 2061-2065.
Betzig et al., "Near-Field Optics: Microscopy, Spectroscopy, and Surface Modification Beyond the Diffraction Limit", Science, vol. 257, No. 5067, Jul. 10, 1992, pp. 189-195.
Betzig, E., "Excitation Strategies for Optical Lattice Microscopy", Optics Express, vol. 13, No. 8, Apr. 18, 2005, pp. 3021-3036.
Ando et al., "An Optical Marker Based on the UV-Induced Green-to-Red Photoconversion of a Fluorescent Protein", PNAS, vol. 99, No. 20, Oct. 1, 2002, pp. 12651-12656.
Axelrod, D., "Total Internal Reflection Fluorescence Microscopy", Methods in Cell Biology, vol. 30, 1989, pp. 245-270.
Izzard et al., "Cell-to-Substrate Contacts in Living Fibroblasts: An Interference Reflexion Study with an Evaluation of the Technique", J. Cell Sci., vol. 21, 1976, pp. 129-159.
Betzig, E. et al. "Imaging Intracellular Fluorescent Proteins at Nanometer Resolution", Science, vol. 313, Sep. 15, 2006, pp. 1642-1645.
Leica Microsystems, "4Pi Microscopy—A Quantum Leap in the 3D Resolution of Fluorescence Microscopy", Research Newsletter-European Edition [online], Jan. 2006, pp. 1-23.
Moerner et al., "Methods of Single-Molecule Fluorescence Spectroscopy and Microscopy", Review of Scientific Instruments, vol. 74, No. 8, 2003, pp. 3579-3619.
Gustafsson et al., "Sevenfold Improvement of Axial Resolutin in 3D Widefield Microscopy Using Two Objective Lenses", Proc SPIE, vol. 2412, Mar. 23, 1995, pp. 147-156.
Abercrombie et al., "The Locomotion of Fibroblasts in Culture: IV. Electron Microscopy of the Leading Lamella", Experimental Cell Research, vol. 67, No. 2, Aug. 1971, pp. 359-367.
Egner et al., "Fast 100-nm Resolution Three-Dimensional Microscope Reveals Structural Plasticity of Mitochondria in Live Yeast", PNAS, vol. 99, No. 6, Mar. 19, 2002, pp. 3370-3375.
Frankel et al., "Revealing the Topography of Cellular Membrane Domains by Combined Atomic Force Microsocpy/Fluorescence Imaging", Biophysical Journal, vol. 90, No. 7, Apr. 2006, pp. 2404-2413.
Osborn et al., "Individual Microtubules Viewed by Immunofluorescence and Electron Microscopy in the Same PtK2 Cell", J. Cell Biology, vol. 77 No. 3, Jun. 1, 1978, pp. R27-R34.
Rust et al., "Sub-Diffraction-Limit Imaging by Stochastic Optical Reconstruction Microscopy (STORM)", Nature Methods, vol. 3, No. 10, Oct. 2006, pp. 793-795.
Hess et al., "Ultra-High Resolution Imaging by Fluorescence Photoactivation Localization Microscopy", Biophysical Journal, vol. 91, No. 11, Dec. 2006, pp. 4258-4272.
Kao et al., "Tracking of Single Fluorescent Particles in Three Dimensions: Use of Cylindrical Optics to Encode Particle Position", Biophysical Journal, vol. 67, No. 3, Sep. 1994, pp. 1291-1300.
Oijen et al., "3D Super-Resolution by Spectrally Selective Imaging", Chemical Physical Letters, vol. 292, No. 1-2, Jul. 31, 1998, pp. 183-187.
Bhushan et al., "Measurement of Surface Topography of Magnetic Tapes by Mirau Interferometry", Applied Optics, vol. 24, No. 10, May 15, 1985, pp. 1489-1497.
Hell et al., "Fundamental Improvement of Resolution with a 4Pi-Confocal Fluorescence Microscope Using Two-Photon Excitation", Optics Communications, vol. 93, No. 5-6, Oct. 1992, pp. 277-282.
Braun et al., "Fluorescence Interferometry of Neuronal Cell Adhesion on Microstructured Silicon," The American Physical Society, Physical Review Letters, vol. 81, No. 23, Dec. 7, 1998, pp. 5241-5244.
Supplementary European Search Report issued by European Patent Office on Jul. 9, 2014 in counterpart application EP 07866170.9, 10 pages.

\* cited by examiner

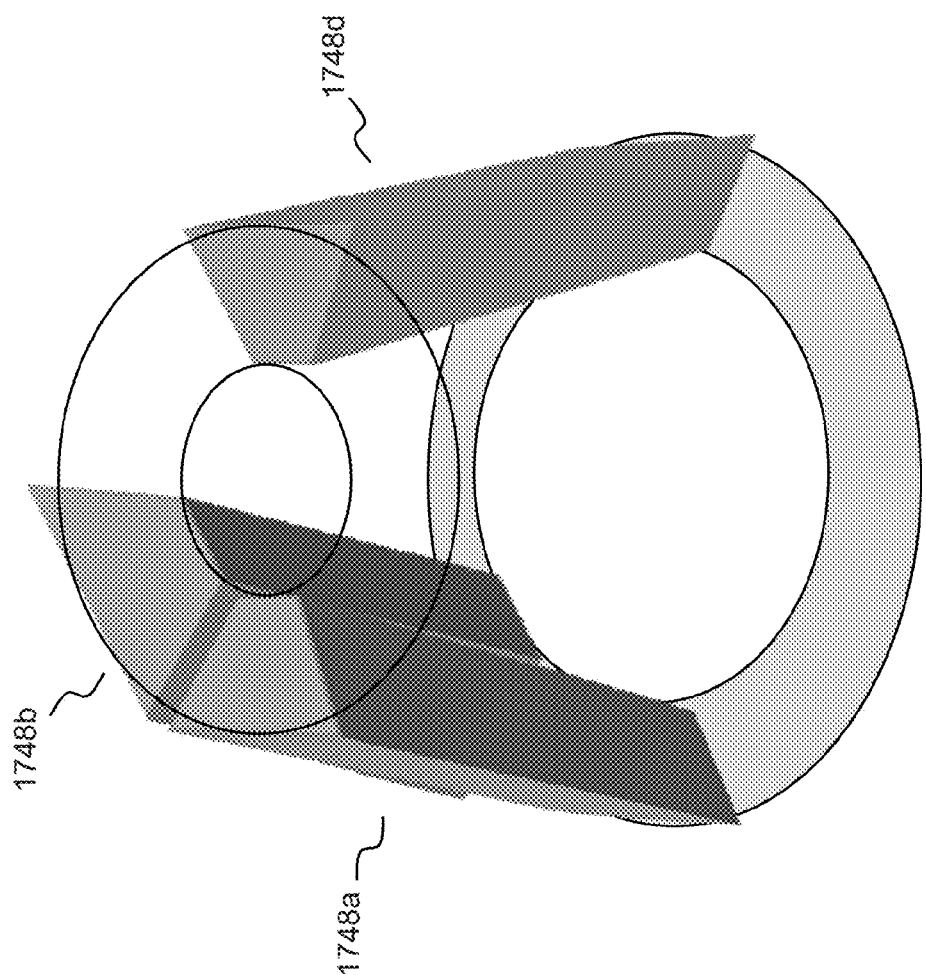

METHODS FOR 3-DIMENSIONAL INTERFEROMETRIC MICROSCOPY

CROSS-REFERENCE TO RELATED APPLICATIONS

This application is a divisional of U.S. application Ser. No. 14/302,153, filed on Jun. 11, 2014, entitled "Method of 3-Dimensional Imaging of Activated Samples," which is a continuation of U.S. application Ser. No. 13/051,670, filed on Mar. 18, 2011, and issued on Jun. 15, 2014 as U.S. Pat. No. 8,780,442, entitled "Optical Interfering Apparatus," which is a divisional of U.S. application Ser. No. 11/961,601, filed on Dec. 20, 2007, and issued on Mar. 29, 2011 as U.S. Pat. No. 7,916,304, entitled "Systems and Methods for 3-Dimensional Interferometric Microscopy," which claims priority to U.S. Application No. 60/871,366, filed on Dec. 21, 2006, entitled "System and Methods for 3-Dimensional Interferometric Microscopy," and to U.S. Application No. 60/908,307, filed on Mar. 27, 2007, entitled "System and Methods for 3-Dimensional Interferometric Microscopy," the disclosures of each of which are hereby incorporated herein by reference in their entirety.

BACKGROUND

The invention relates generally to interferometric microscopy including, for example, interferometric microscopy of samples comprised of or labeled with spatially resolvable point sources such as samples that internally radiate light from photo-activated fluorescent protein molecules and/or interferometric microscopy where a phase difference is measured to determine position information in the third dimension (e.g., the z coordinate) while simultaneously measuring position information in the two other dimensions (e.g., the x and y coordinates).

Microscopy systems that measure interferometric phase are known. For example, one known microscopy system measures interferometric phase by illuminating an extended surface of an object with an external light source. Light reflected from the sample interferes with a reference beam in a beam splitter. The interfered beam is imaged onto a detector. The optical path difference between the reference beam and the sample beam can modulate the amplitude of the output interfered beam and provide a measure of an object height.

Also known are microscopy systems that interfere two beams from a sample via opposing objectives to measure only one interfered output beam. Such microscopy systems do not explicitly measure phase. These microscopy systems can resolve structure in the axial dimension.

Such known microscopy systems, however, suffer several disadvantages. For example, such systems cannot be applied to fluorescently-labeled samples that are common in biology because the internally-supplied fluorescent radiation has no useable phase relation with respect to any externally-supplied reference beam used for excitation of fluorescence. Without a reference beam, interference is not achievable. In addition, a single or sequentially phased interferometric measurement cannot be used to separate interferometric phase from amplitude if the radiation is transient or strongly time variant, such as is the case in blinking fluorescent molecules or other single photon sources. Thus, no quantitative measure of phase and positional information can be derived from a single interferometric measurement or a time sequence of measurements. Finally, lateral resolution for far-field interferometric systems is limited by the Abbe diffraction length $\lambda/2NA$, where is the wavelength and NA is the numerical aperture. Thus, a need exists for an improved microscopy system.

SUMMARY

In one embodiment, an apparatus comprises an optical system with multiple detectors and a processor. The optical system is configured to produce images of an optical source in a first dimension and a second dimension substantially orthogonal to the first dimension at each detector at a given time. Each image from the images is based on an interference of an emission from the optical source in a first direction and an emission from the optical source in a second direction different from the first direction. The processor is configured to calculate a position in a third dimension based on the images. The third dimension is substantially orthogonal to the first dimension and the second dimension.

In some embodiments, molecules of interest that are tagged with fluorescent labels can be localized in 3 dimensions to an accuracy better than the diffraction limit. In such embodiments, the phase information associated with the image can be used to determine information about the position of a molecule in the z coordinate such that a 3D (three-dimensional) representation with sub-diffractive accuracy $<<\lambda/2$ in the 3 dimensions can be achieved. In other words, information about the position of a molecule in the third dimension (e.g., the z coordinate) can be obtained while information about the position of the molecule in the two other dimensions (e.g., the x and y coordinates) can be obtained.

BRIEF DESCRIPTION OF THE DRAWINGS

FIG. 21 shows a perspective view of three out of the six prism components of the annular expander shown in FIG. 17.

DETAILED DESCRIPTION

Figure 1:
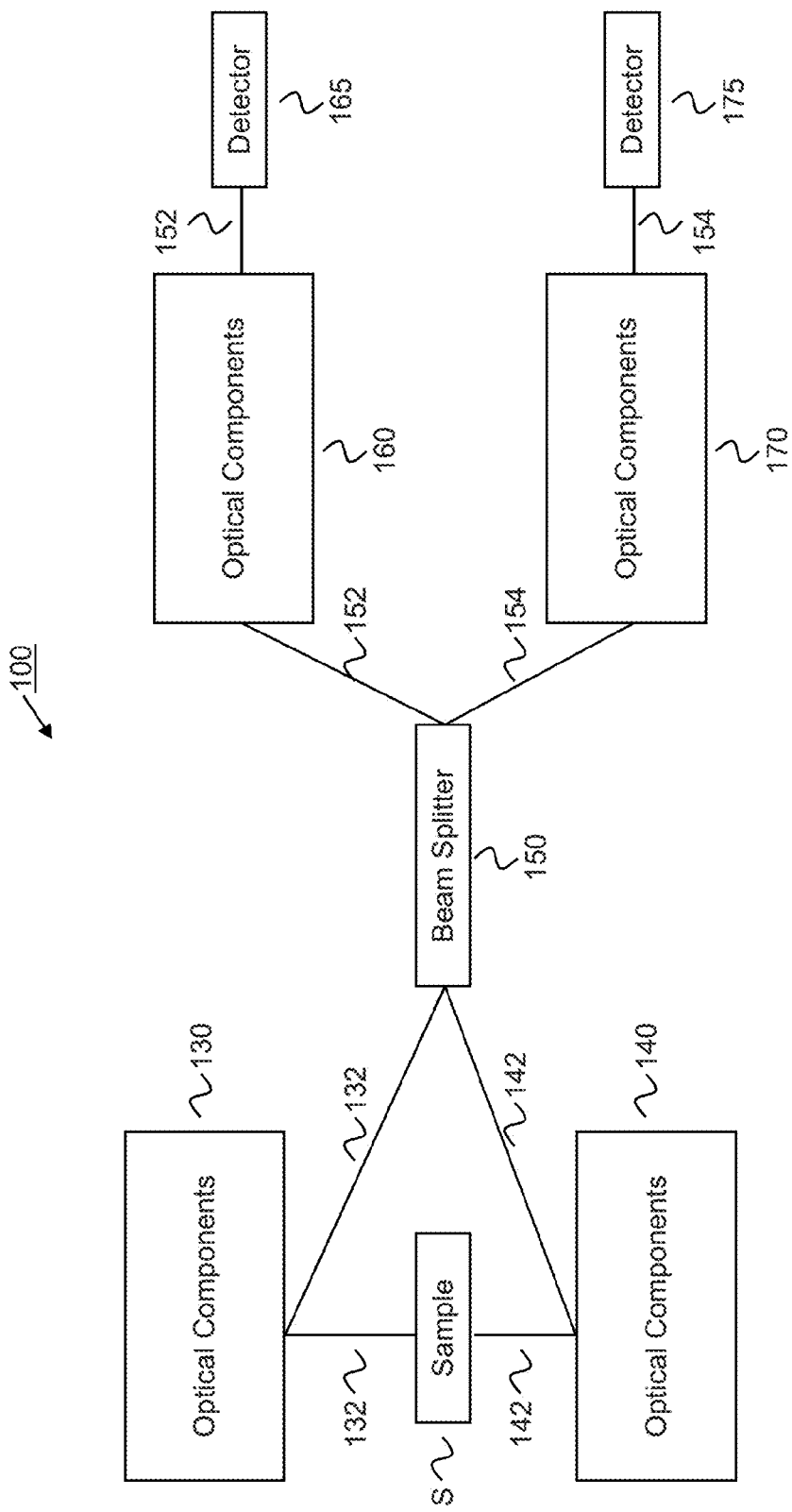
FIG. 1 shows a system block diagram of a two-phase interferometric microscopy system and a sample, according to an embodiment of the invention.

In broad terms, one or more embodiments described herein can produce 3-dimensional renderings with resolution better than known optical microscopy. In some embodiments, an interferometric microscope can measure a phase difference to determine position information in the third dimension (e.g., the z coordinate) while simultaneously measuring position information in the two other dimensions (e.g., the x and y coordinates). In some embodiments, an interferometric microscope can measure samples containing a collection of point-sources such as samples that internally radiate light from photo-activated fluorescent labels.

For example, 3-dimensional renders of specific labeled proteins in a sample can be produced. Contrast can be given by specific labeled proteins and still be acquired with a specialized optical microscope. For example, one or more embodiments can be used to locate a fluorescently labeled protein in a cell with full 3D location.

One known microscopy system is the Photo-Activated Localization Microscopy ("PALM") system. This PALM system is described in the following references, which are incorporated herein by reference: U.S. Patent Application Ser. No. 60/683,337, entitled "Optical Microscopy with Phototransformable Optical Labels" and filed May 23, 2005; U.S. Patent Application Ser. No. 60/780,968, entitled "Imaging Intracellular Fluorescent Proteins at Near-Molecular Resolution" and filed Mar. 10, 2006; PCT Patent Application Serial No. PCT/US2006/019887, entitled "Optical Microscopy with Phototransformable Optical Labels," filed May 23, 2006 and published on Nov. 11, 2005 as PCT Publication No. WO/2006/127682; Betzig, E. et al., "Imaging Intracellular Fluorescent Proteins at Nanometer Resolution," Science, Vol. 313, Sep. 15, 2006; and Betzig, E. et al., "Supporting online Material for 'Imaging Intracellular Fluorescent Proteins at Nanometer Resolution'," Science Express, Aug. 10, 2006, [online] www.sciencemag.org/cgi/content/full/1127344/DC1 (collectively referred to herein as the "Betzig references").

The PALM system localizes molecules predominantly in 2 dimensions, in the x,y image plane, to provide high-resolution images that exceed that of diffraction-limited microscopes. One known way to obtain information about the location of labeled molecules in the third dimension involves a serial process such as taking data on several sections, or by quantifying the point spread function variations of defocused molecules that depend on the distance to the focal plane.

As with 2D PALM system, switchable optical labels here can be the photo activatable fluorescent proteins such as PA-GFP. PA-GFP is a photo activatable fluorescent protein mutant of GFP where irradiation with 405 nm light can transform it from a non-fluorescent version into an anionic form that absorbs excitation radiation at 500 nm and emits fluorescent radiation at 520 nm. Other photo-activatable proteins are Dronpa, Eos, Kaede, Kikume, Kindling-FP, PA-CFP, many of which are useable in monomeric, dimeric and tetrameric forms. Such proteins can be genetically expressed and genetically attached to label a protein of interest. This enables protein specific images to be constructed. Various caged dye molecules can also be used but they typically require immuno-labeling or alternate attachment schemes. Because some of these proteins/labels have sufficiently different photophysical properties such as emission wavelength, excitation wavelength or bleaching rates, that it is possible to make images with two different switchable optical labels. In this case, the addition of dichroic mirrors in the beam paths can result in a new second or even third set of images for this 3D interferometric microscopy. Sequencing the acquisition to image and bleach one protein and then image the second is another way to image different labeled proteins.

Some embodiments described herein, however, use the phase angle information of the optical path length difference such that both two-dimensional intensity image, from which the x,y position of labeled molecules can be determined, and the phase dependent images, from which the z position of the labeled molecules can be determined, can be simultaneously acquired and can be reconstructed. In other words, two or more emission beams from a sample are further split into two or more beams and pairwise interfered with each other (based on their differing phases) and the resulting interfered beams form images that are recorded simultaneously to reconstruct the phase of the path length difference (i.e., the z position) of the localized sources of a sample. In addition, in some embodiments, the interference amplitude can also be extracted and used as a supplemental measure of vertical position.

Such embodiments are advantageous in many respects. For example, as mentioned above, in some embodiments described herein, the phase difference can be measured to determine position information in the third dimension (e.g., the z coordinate) while simultaneously measuring position information in the two other dimensions (e.g., the x and y coordinates). This allows for a measurement of all three dimensions that can be more accurate than known systems where these measurements occur at different times. Such a measurement technique described herein can be particularly advantageous, for example, for samples that are not static such as photo-activated samples that have a time-varying brightness.

As also mentioned above, in some embodiments described herein, the component of the sample being measured is separable and identifiable as a sub-diffractive sized point source. This allows for a measurement that can be well defined and more accurate than known systems where the measured sample component is an extended source with a distribution of positions and various portions of the source can interfere with other portions of the source. Such a measurement technique described herein can be particularly advantageous for performing measurements with an accuracy below the diffraction limit.

FIG. 1 shows a system block diagram of a two-phase interferometric microscopy system and a sample, according to an embodiment of the invention. As shown in FIG. 1, the microscopy system 100 includes optical components 130 and 140, a beam splitter 150, optical components 160 and 170, and detectors 165 and 175.

The optical components 130 and 140 can be any type of optical component(s) that define an optical path 132 and 142, respectively, from the sample S to the beam splitter 150. For example, optical components 130 and 140 each can include a set of mirrors, lenses or objectives. The optical components 130 and 140, for example, can include lenses or objectives that collimate optical energy emitted from the point source of the sample. Although FIG. 1 shows two diametrically opposite paths 132 and 142 into two optical components 130 and 140, in some embodiments discussed below, a single optical component such as optical component 140 can encompass two non-opposing paths 132 and 142.

Optical components 130 and/or 140 can include additional components and/or features that allow the sample S to receive one or more sources of activation. For example, in some embodiments, optical energy from optical sources (not shown in FIG. 1) can be used to activate the fluorescent response of the sample S to excitation photons. In such embodiments, for example, the optical components 130 and/or 140 can include an aperture through which optical energy from the optical sources can irradiate the sample S while minimizing stray radiation from the excitation laser traveling back towards the detectors 165 and/or 175. Laser line filters can also be in the beam path to the detectors 165 and/or 175 so that predominantly fluorescent light reaches the detectors. A first laser source can radiate the sample S, for example, with an activation beam and a second laser source can radiate the sample S, for example, with an excitation beam. In other embodiments, an optical source other than a laser, such as a light-emitting diode, incandescent lamp, can be used as the source for activation and/or excitation. As described in further detail in the Betzig references incorporated by reference above, the activation beam is configured to activate sufficiently sparse subsets of individually resolvable photo-activatable labels in the sample, and the excitation beam is configured to excite the activated portions of the sample S to emit fluorescence-based photons.

In alternative embodiments, the fluorescent response of the sample can be activated with one or more chemicals. In such alternative embodiments, the sample can be exposed to a first chemical to activate the fluorescent sparse subsets of molecules of the sample and subsequently to a second chemical to deactivate the fluorescence of the sample if photo-bleaching is not used.

The beam splitter 150 can be any type of appropriate optical component that receives and combines the optical energy along optical paths 132 and 142, and sends the combined and mixed optical energy along optical paths 152 and 154 (each also referred to herein as "a leg") to optical components 160 and 170. For example, beam splitter 150 can be a 50:50 beam splitter where the combined optical energy is split such that substantially 50 percent of the combined optical energy is sent on optical path 152 and substantially 50 percent of the combined optical energy is sent on optical path 154. As optical energy from optical paths 132 and 142 is interfered and mixed by the beam splitter 150, the resulting optical energy along optical path 152 is based on a relative phase difference between the optical energies from optical paths 132 and 142. Similarly, as optical energy along optical paths 132 and 142 is interfered and mixed in the beam splitter 150, the resulting optical energy along optical path 154 is based on a relative phase difference between the optical energies from optical paths 132 and 142, which is different from the relative phase difference associated with the optical energy along optical path 152. In this embodiment, the resulting optical energy along optical path 152 and optical energy along optical path 154 differ in phase by approximately 180 degrees. Alternatively, beam splitter 150 can divide the beam into any desired proportions such as 66:33, 70:30, etc. In yet another embodiments, beam splitter 150 can be a combination of multiple beam splitters. Such beam splitters can be constructed, for example, from a block of two glass segments and a thin film coating disposed between the two glass segments. Such beam splitters could produce three or more outputs, i.e., more than the two of 152 and 158. This enables three or more output beams to be expressed with three or more interference phase angles (e.g., 0 degrees, 120 degrees and 240 degrees), rather than 0 and 180 degrees in the two beam cases. In yet other embodiments, in addition to or alternative to a beam splitter having a thin film coating, diffractive gratings can be used as beam splitters and can divide a beam into two or more beams. Gratings can also take multiple input beams and mix and interfere them into various output beams. In some embodiments, the diffraction gratings can be used in conjunction with a sample having point sources emitting at the substantially same wavelength such as a label having a switchable scattering center (e.g., a photoswitchable label with an activatable scattering characteristic). Such a sample having point sources emitting at substantially the same wavelength advantageously allows the diffraction gratings to deflect input beams at a relatively narrow deflection angle, which is a function of the wavelength of the input beam.

In another embodiment, one or more of the beam splitters can include striped mirror portions instead of diffraction gratings or thin-film coatings. In one embodiment, the striped mirror portions have a stripe period that is sufficiently small such that the diffractive order does not refocus into the image plane. For a wavelength focal length f, and image size d, this means a period less than fλ/d. Other patterns could be used such as square or hexagonal polka dots. To prevent ghosting in the image, however, the same condition of the polka dot period (i.e., less than fλ/d) must be maintained.

Similar to optical components 130 and 140, optical components 160 and 170 can be any type of optical component(s) that defines an optical path 152 and 154, respectively, from the beam splitter 150 to the detectors 165 and 175, respectively. For example, optical components 160 and 170 can be lenses that de-collimate optical energy from optical paths 152 and 154, respectively, so that the optical energy is focused at detectors 165 and 175, respectively. In some embodiments, one or more of the optical components such as optical components 130, 140, 160 and 170, and/or beam splitter 150 can include adaptive optics.

In use, a statistically sparse subset of separately-imaged labels in the sample S is activated before a measurement is made. As mentioned above, the statistically sparse subset of the labels in the sample S can be activated by an appropriate technique such as by photo activation or chemical activation. Once activated, the sample S can be excited by an excitation source such as a laser. This results in photons being emitted from the sample S along optical paths 132 and 142 through optical components 130 and 140 to beam splitter 150. The optical energy from optical paths 132 and 142 are combined at beam splitter 150 and sent along paths 152 and 154 through optical components 160 and 170 to detectors 165 and 175, respectively. A phase difference between the beams 132 and 142 causes interference and modulates the intensity of the detected signals at detectors 165 and 175, which can used to determine a position in the z coordinate, as described below in further detail. In addition, the detected signals at detectors 165 and 175 also provide position information in the x, y coordinates. After the detected signals are collected, the activated sparse subsets of the labels in the sample S can be bleached by repeated excitation so that no further optical signals can be detected from those labels, and further sparse subsets of labels can then be activated and excited for additional measurements, and the process repeated.

Figure 2:
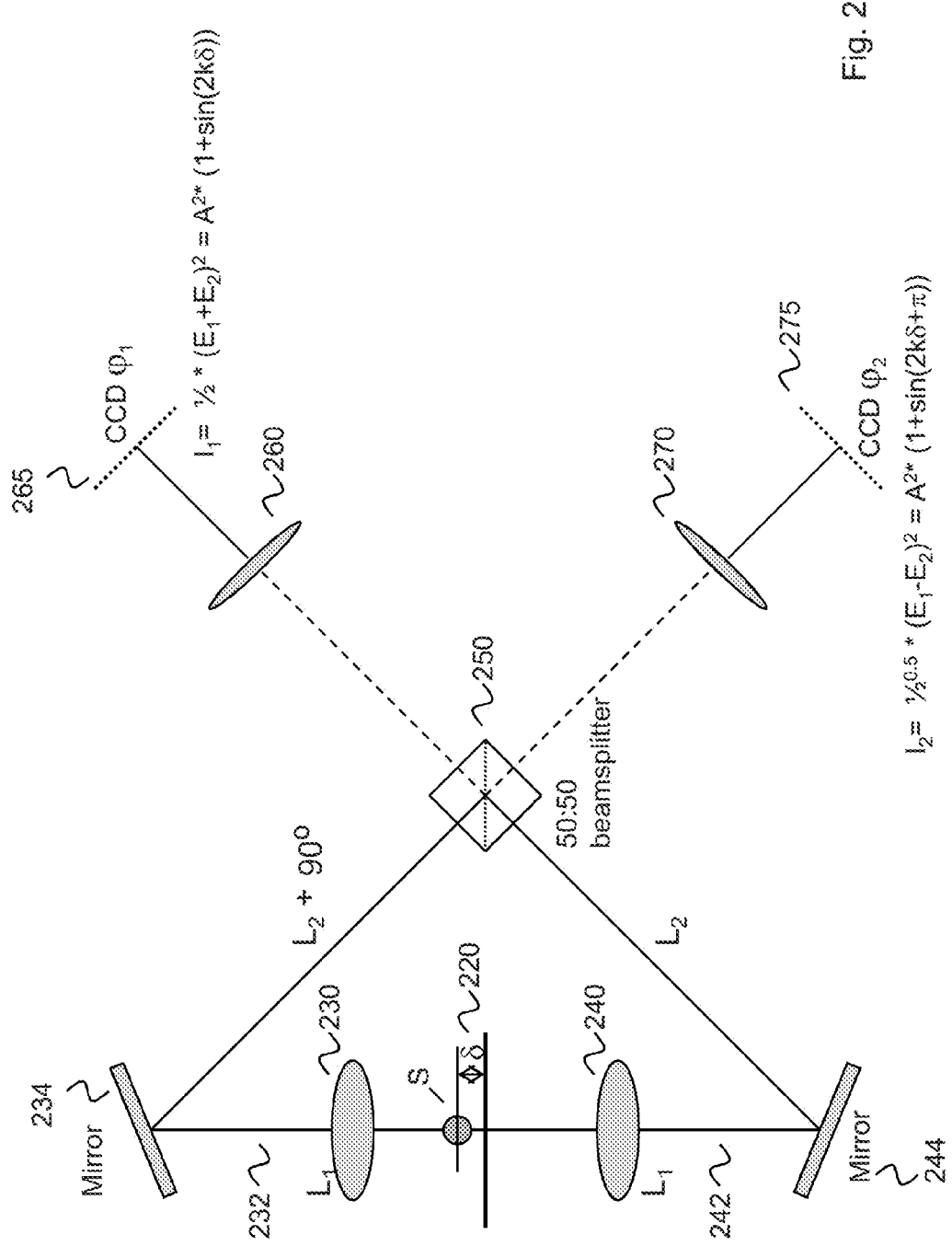
FIG. 2 shows a system block diagram of a two-phase interferometric microscope system and a single emitter sample, according to an embodiment of the invention.

FIG. 2 shows a system block diagram of a two-phase interferometric microscopy system and a sample with a single active emitter, according to an embodiment of the invention. As shown in FIG. 2, a single quantum emitter S is located a distance, δ, from a center location 220. The single quantum emitter S can be, for example, a fluorescent molecule, a quantum dot or a sub-wavelength scattering center. A radiated photon can escape from the quantum emitter S both upwards into lens 230 and downwards into the lens 240, where two collimated beams 232 and 242, respectively, are formed. The collimated beams 232 and 242 reflected by mirrors 234 and 244, respectively, and are received at beam splitter 250.

Two beam paths are defined: a first beam path (also referred to as the top path) from the quantum emitter S to mirror 234 and from mirror 234 to beam splitter 250; and a second beam path (also referred to as the bottom path) from the quantum emitter S to mirror 244 and from mirror 244 to beam splitter 250. The mirrors 234 and 244 and beam splitter 250 are positioned relative to the quantum emitter S such that the lengths of the beam paths are matched to about a wavelength $(L_1+L_2)_{top}=(L_1+L_2)_{bottom}$, with the exception of a positional displacement δ of the emitter and a 90 degree phase shift on the top beam path, where $L_1$ is the path length between the center location 220 and the mirrors 234 or 244, and $L_2$ is the path length between the mirrors 234 or 244 and the beam splitter 250. In this case the electric field of the optical beam in the top beam path is:

$$E_1 = A^* \exp(-ik\delta + ikL_1 + ikL_2 + i\pi/2),$$

where $k=2\pi/\lambda$.

The electric field of the optical beam in the bottom beam path is:

$$E_2 = A^* \exp(ik\delta + ikL_1 + ikL_2).$$

When received at the beam splitter 250, the optical beams are combined and transmitted to the two detectors 265 and 275 through lenses 260 and 270, respectively. The electric field from one source of the optical beam going towards each detector 265 and 270 is: a wavelength of λ=600 nm, the positional information can be determined to less than 1 radian, which corresponds to δ=50 nm. Such an interferometric system can be configured such that the x,y locations of the source emitters can also be measured to the nanometer scale resolution.

Figure 3:
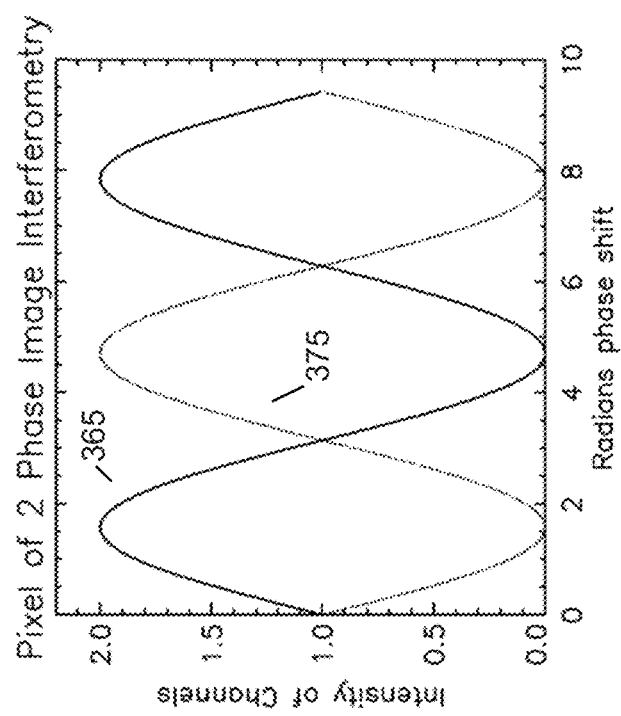
FIG. 3 shows a graph of the intensities of the radiated light detected at the two detectors of FIG. 2.
Figure 4:
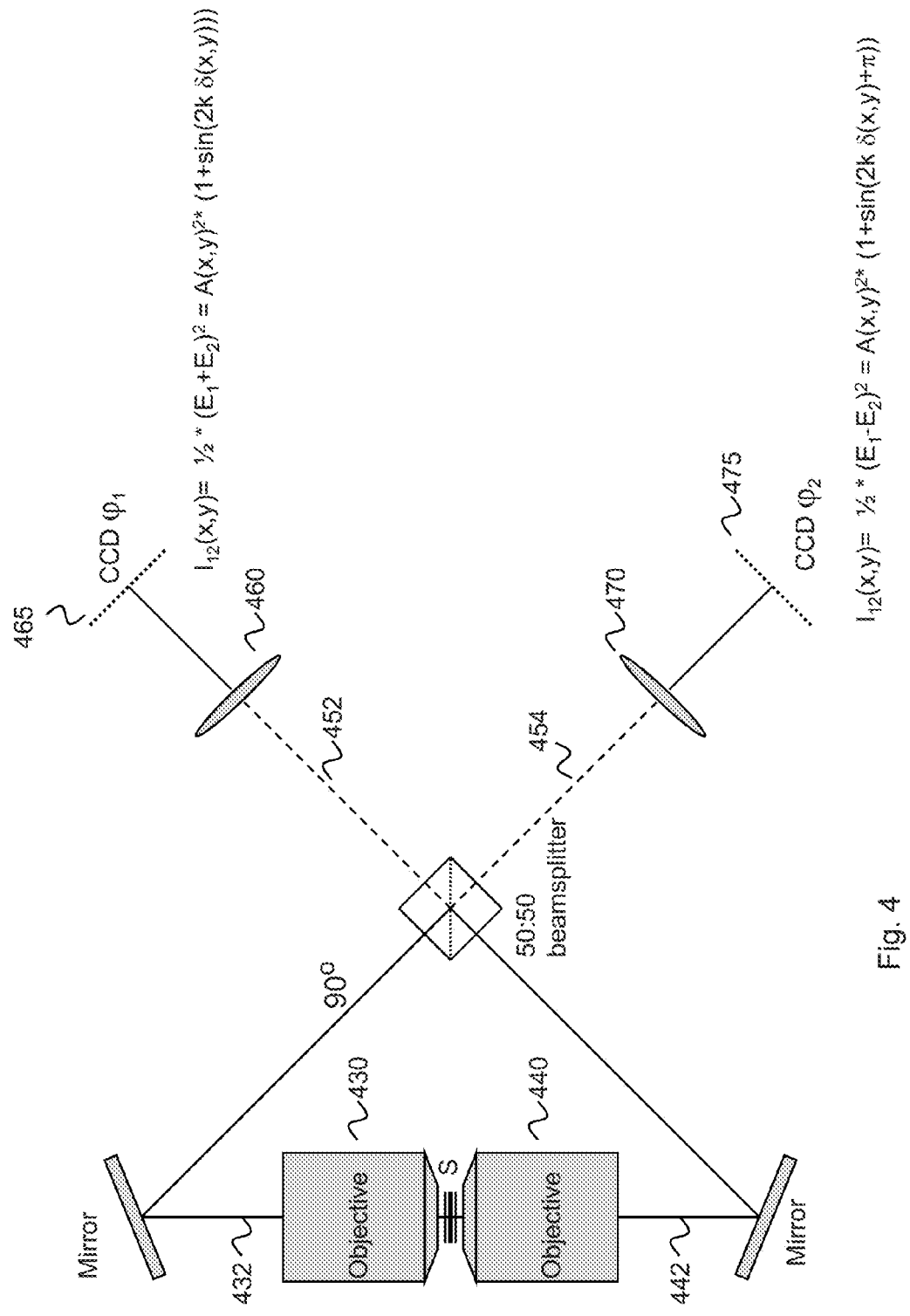
FIG. 4 shows a system block diagram of a two-phase interferometric microscope system and an extended sample, according to an embodiment of the invention.
Figure 5:
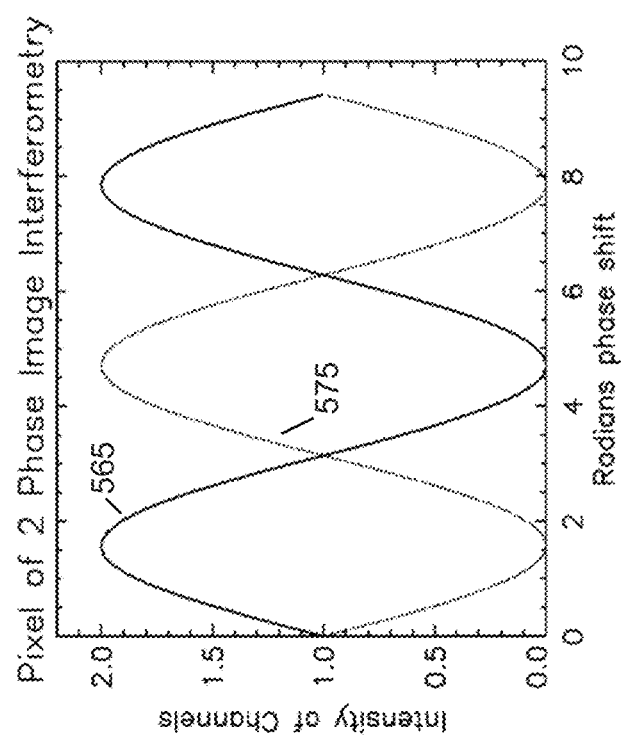
FIG. 5 shows a graph of the intensities of the radiated light detected at the two detectors of FIG. 4.

The thickness of the sample can affect the extent to which a unique z-coordinate position can be determined. For example, in the two-phase embodiments shown in FIG. 2 or 4, if the thickness of the sample 210 is less than λ/4, then a unique z-coordinate position can be determined. The sensitivity to the displacement, δ, for these embodiments is non-uniform. In other words, if the phase is such that intensity is determined close to the minimum or maximum of the sine wave, then the slope approaches zero and therefore the sensitivity approaches to zero as shown in FIGS. 3 and 5. If, however, the phase is such that the intensity is determined away from the minimum or maximum of the sine wave, then the sensitivity to the displacement, δ, for these embodiments is measurable and nonzero.

Figure 6:
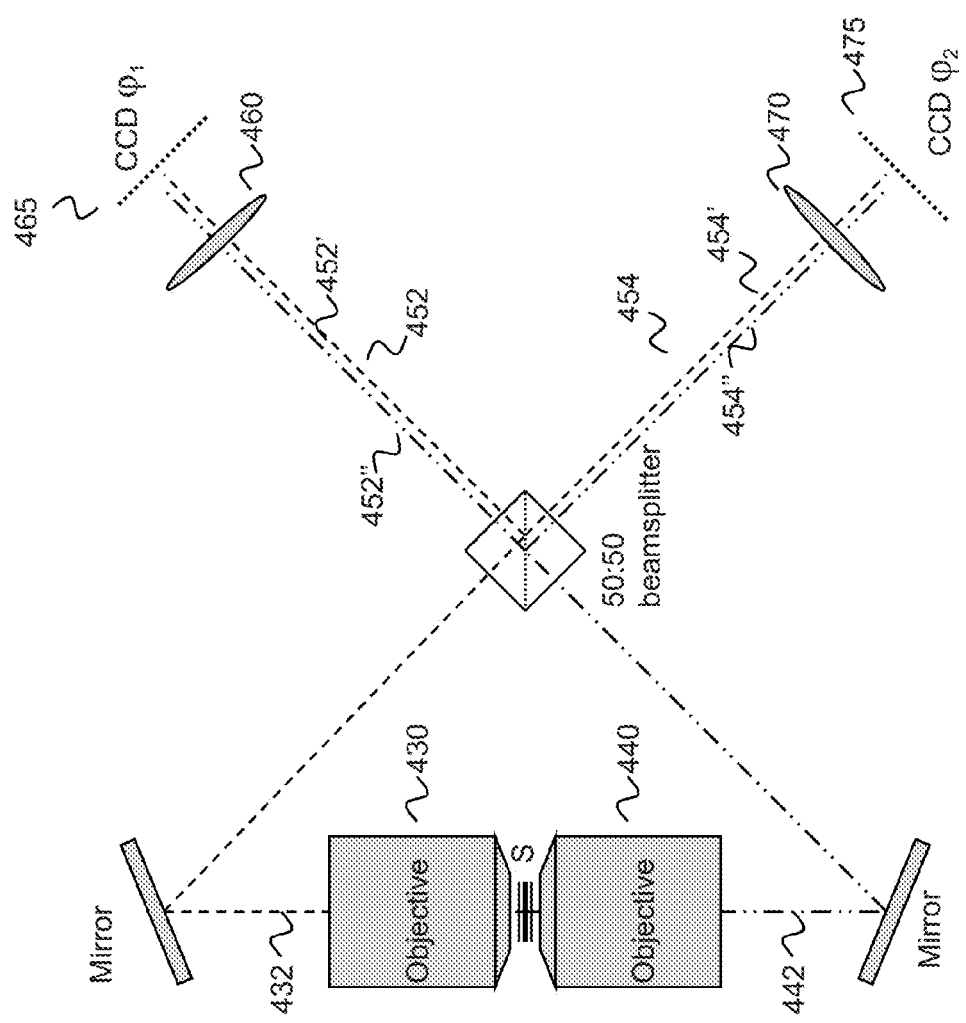
FIG. 6 shows a system block diagram of a two-phase interferometric microscope system with representations of beam phases, according to an embodiment of the invention.

FIG. 6 shows a system block diagram of a two-phase interferometric microscope system with representations of beam phases, according to an embodiment of the invention. Beam 432 has a phase different from the phase of beam 442 and output beam 452 includes components 452' and 452" which differ in phase. Although beam components 452' and 452" are shown as being separated in FIG. 6, this is for illustration purposes and it should be understood that the beam components are coincidental and interfering with each other. Beam component 452' originates from beam 432 and beam component 452" originates from beam 442. Similarly, output beam 454 includes components 454' and 454" which differ in phase. Although beam components 454' and 454" are show as being separated in FIG. 6, this is for illustration purposes and it should be understood that the beam components are coincidental and interfering with each other. Beam component 454' originates from beam 432 and beam component 454" originates from beam 442. In this embodiment, the phase difference between beam components 452' and 452" determines an intensity that is detected at detector CCD $\phi_1$ and the phase difference between beam components 454' and 454" determines an intensity that is detected at detector CCD $\phi_2$.

Figure 7A:
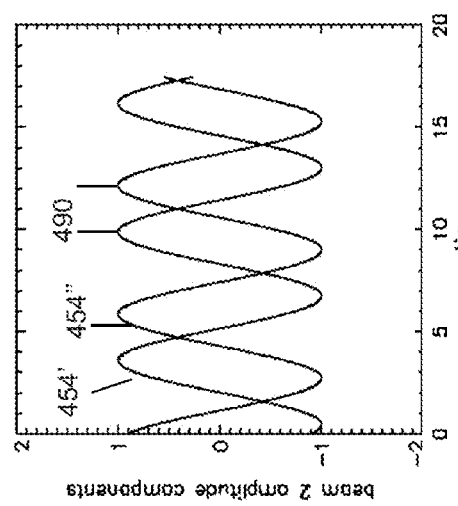
FIGS. 7A and 7B each show a graph displaying the phase of the beam intensities of the components for a given output beam detected at a respective detector of FIG. 6.
Figure 7B:
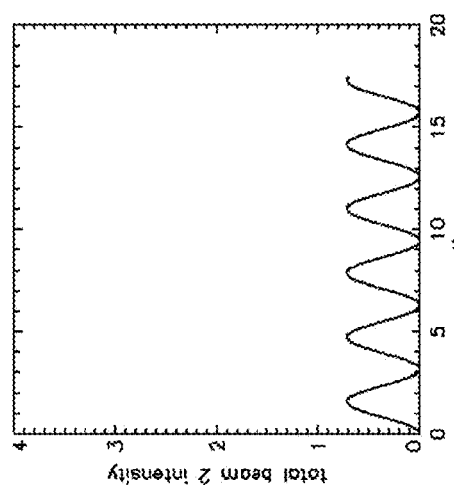
Figure 7C:
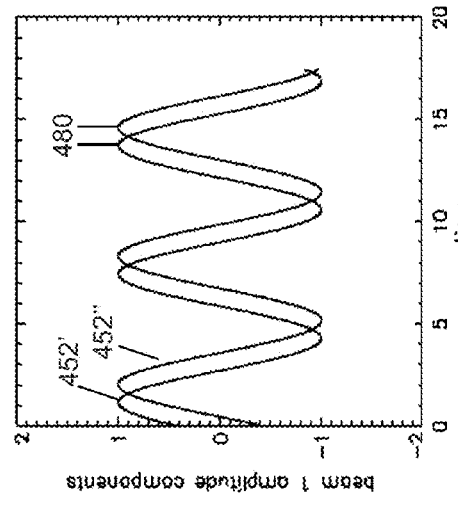
FIGS. 7C and 7D each show a graph displaying the intensities of the output beams associated with FIGS. 7A and 7B, respectively.
Figure 7D:
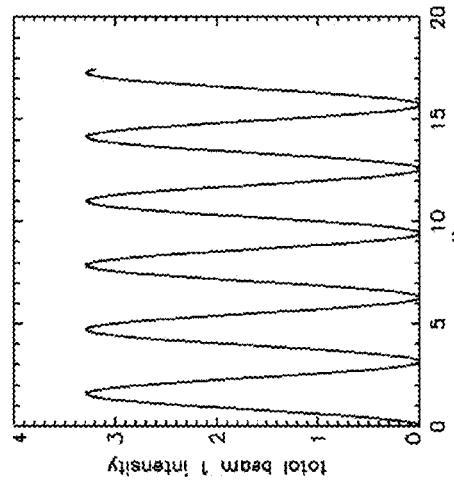

FIGS. 7A and 7B each show a graph displaying the phase of the beam intensities of the components for a given output beam detected at a respective detector of FIG. 6. Output beams 452 and 454 in FIG. 6 include components of input beams 432 and 442. As shown in FIG. 7A, 452' and 452" are components of output beam 452 and are separated in phase by a phase difference 480. As shown in FIG. 7B, 454' and 454" are components of output beam 454 and are separated in phase by a phase difference 490. The difference in these phase differences will vary as a function of the position of the object. The squared sum of the beams represented in FIG. 7A produce a beam with the intensity shown in FIG. 7C, and likewise the squared sum of the beams in represented FIG. 7B produce a beam with the intensity shown in FIG. 7D. The relative intensity of these two beams, $I_1$ and $I_2$, determine the interference phase and thereby the vertical displacement δ.

Figure 8:
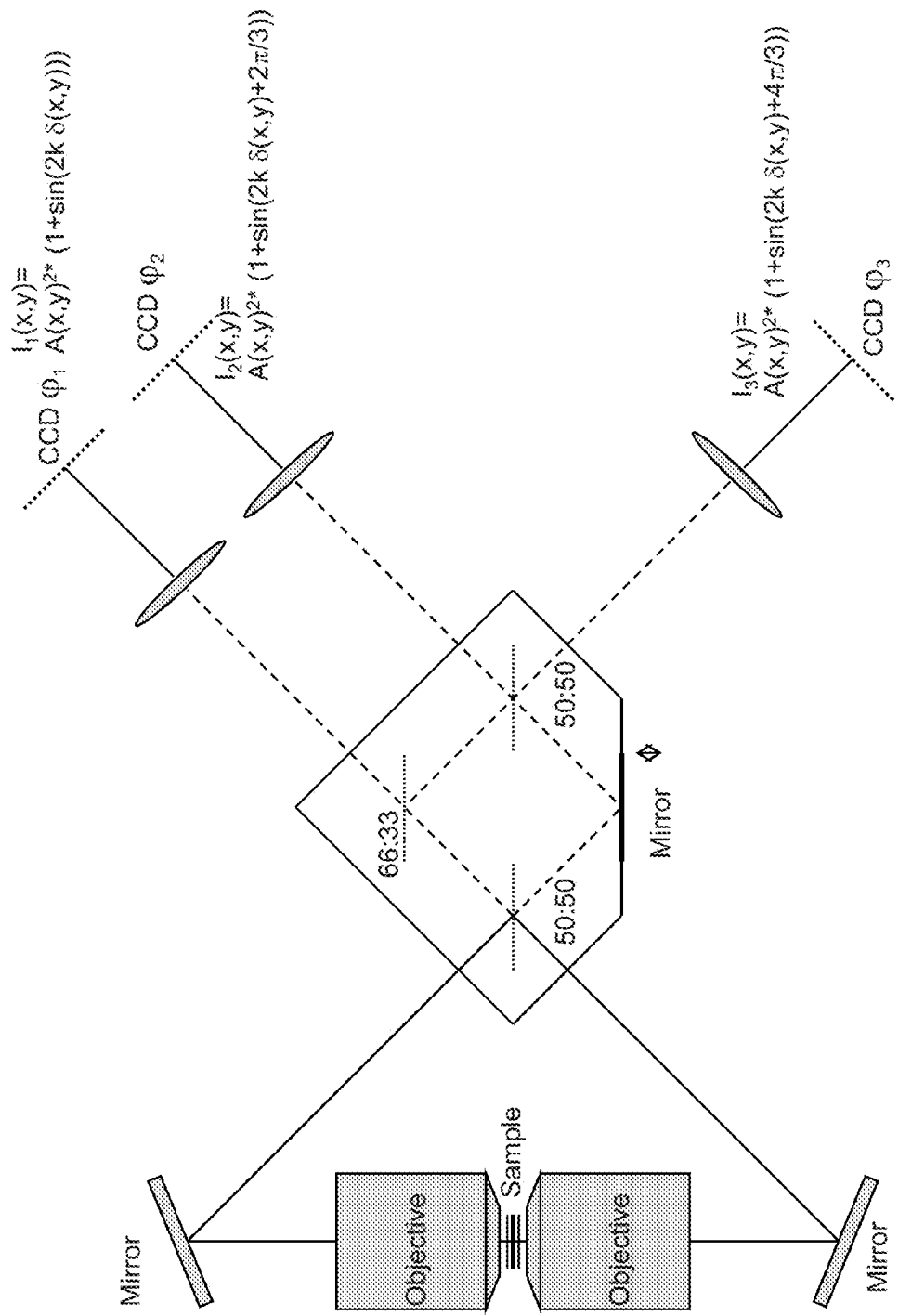
FIG. 8 shows a system block diagram of a three-phase interferometric microscope system, according to an embodiment of the invention.
Figure 9:
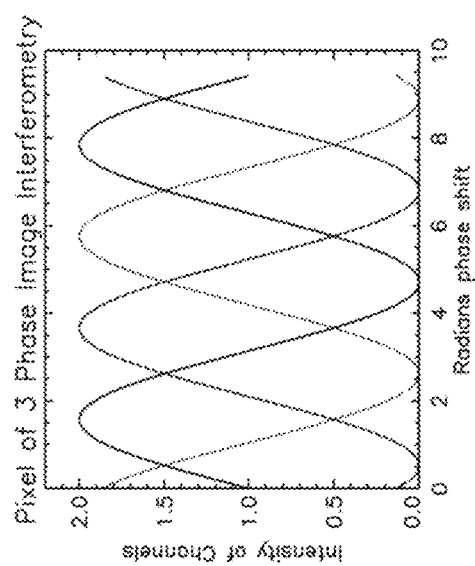
FIG. 9 shows a graph of the intensities of the radiated light detected at the three detectors of FIG. 8.

In alternative embodiments, the interferometric microscopy system can have more than two-phases. For example, FIG. 8 shows a system block diagram of a three-phase interferometric microscopy system, according to an embodiment of the invention. FIG. 9 shows a graph of the intensities of the radiated light from a point source when properly interfered and detected at the three detectors of FIG. 8.

Figure 10:
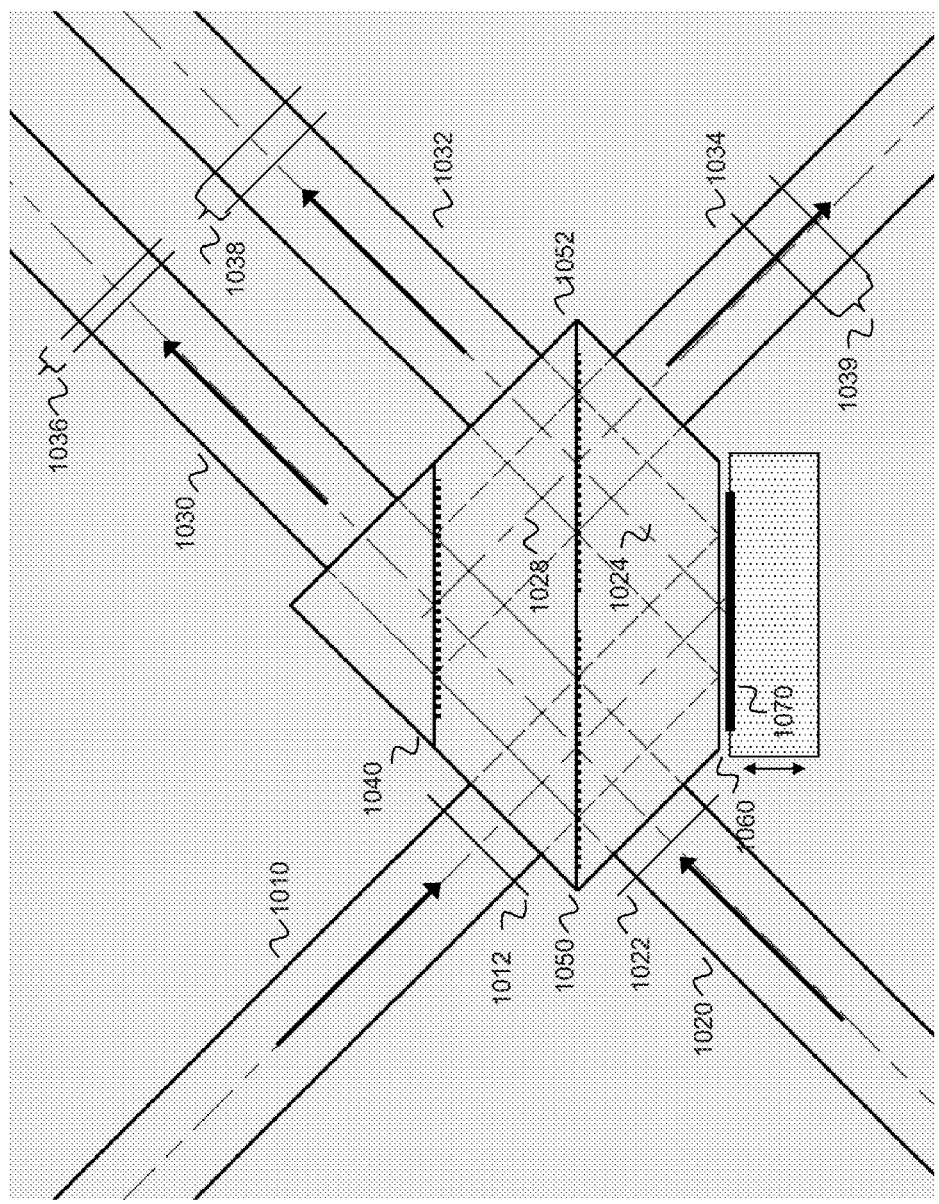
FIG. 10 shows a system block diagram of a three-way beam splitter, according to an embodiment of the invention.
Figure 11:
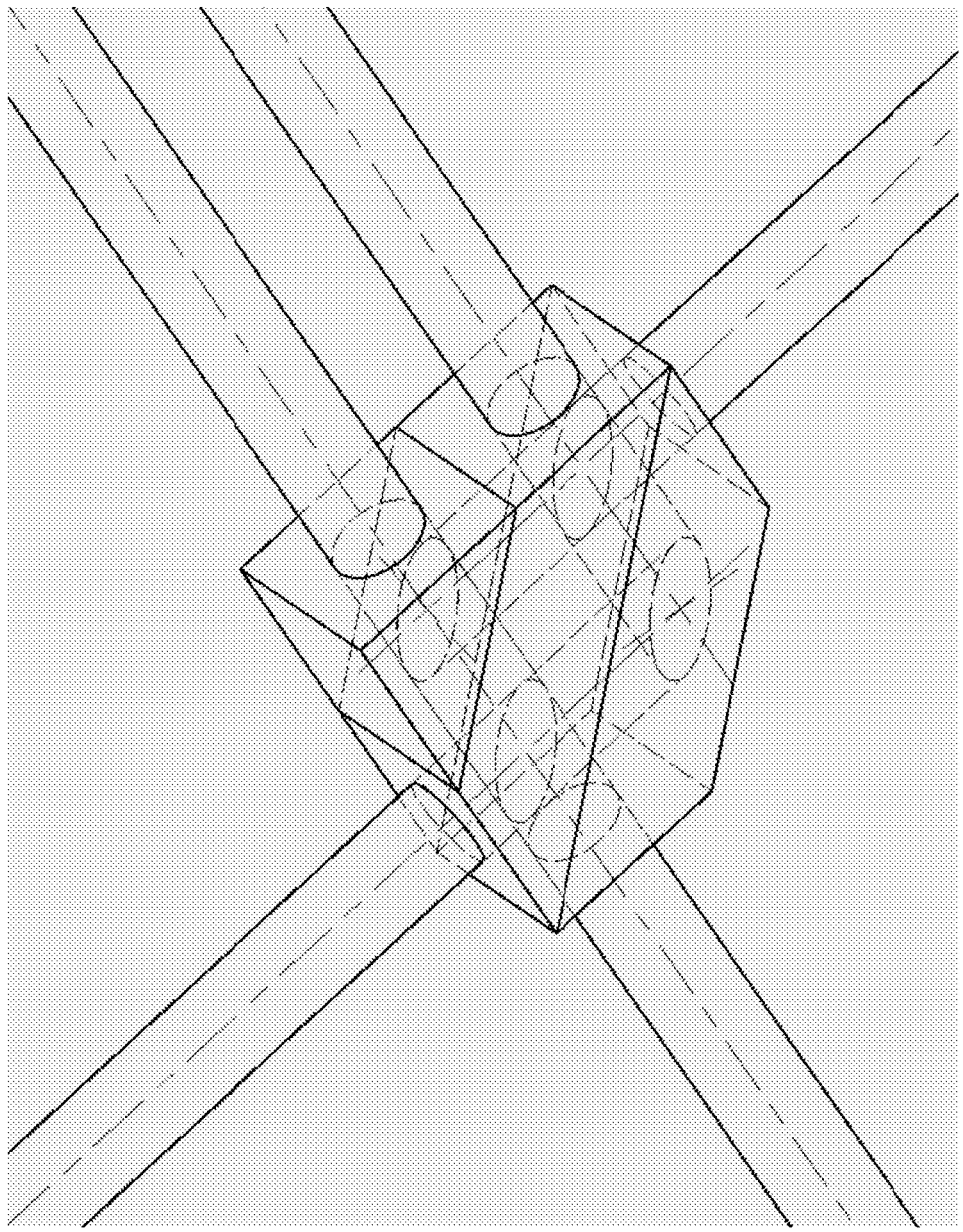
FIG. 11 shows a perspective view of the three-way beam splitter shown in FIG. 10.

FIGS. 10 and 11 show an embodiment of a 3-way beam splitter. The two emission beams 1010 and 1020 enter a 50-50 beam splitting surface 1050. The two resulting interfered beams proceed to an upper 66:33 beam splitting surface 1040 and a lower mirror surface 1070. Most of the upper beam, 66%, exits into output path 1030 and 33% goes to path 1028 and interferes with the beam 1024 that has been reflected from the mirrored surface 1070. This final interference takes place on a 50:50 beam splitting surface 1052 resulting in the second and third output beams 1032 and 1034. To have a balanced 3-way interference (i.e., similar amplitudes for output beams 1030, 1032 and 1034) between the 3 outputs, the phase of the interfering beams 1028 and 1024 can be tuned by changing the position of the mirror 1070 and thereby the gap 1060. The gap 1060 can be filled with index matching oil to minimize residual reflectivity on the bottom of the glass prism.

Figure 10C:
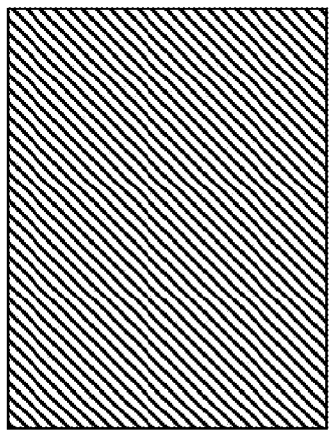
FIGS. 10A, 10B and 10C show striped mirrors used as beam splitting devices in the three-way beam splitter of FIG. 10, according to an embodiment of the invention.
Figure 10B:
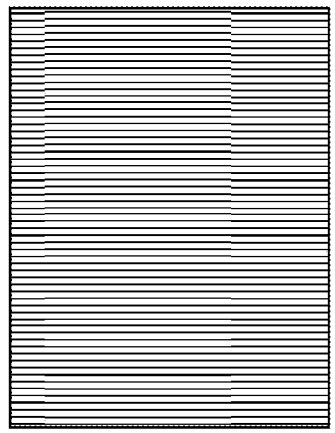
Figure 10A:
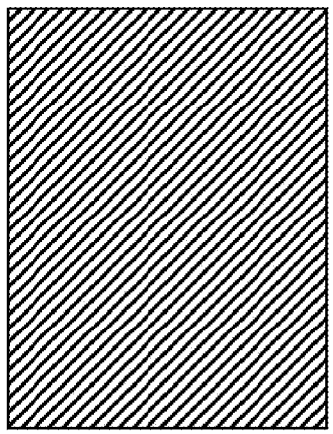

FIGS. 10A, 10B and 10C show striped mirrors used as beam splitting devices in the three-way beam splitter of FIG. 10, according to an embodiment of the invention. Each striped mirror shown in FIGS. 10A, 10B and 10C is rotated with respect to the other striped mirrors shown in FIGS. 10A, 10B and 10C to reduce undesirable interference in the beam paths.

FIGS. 10 and 11 further represent propagation of wavefronts associated with object and image planes through an embodiment of a 3-way beam splitter. Emission beams 1010 and 1020 having wavefronts 1012 and 1022 enter beam splitting surface 1050. Wavefronts 1012 and 1022 are associated with the object plane of the sample and are interfered with each other at beam splitting surface 1050. The resulting wavefronts interfere with each other at beam splitting surfaces 1040 and 1052, as they propagate through the 3-way beam splitter. Beam splitting surfaces 1040, 1050 and 1052 have sufficient surface area to accommodate distortion or spreading of the wavefronts during interference at beam splitting surfaces 1040, 1050 and 1052. Output beams 1030, 1032 and 1034 emerge from the 3-way beam splitter having combined the beams 1010 and 1020 with a relative phase shift of 1036, 1038 and 1039. The results in different intensities of beams 1030, 1032 and 103, which are intact, interfered versions of wavefronts 1012 and 1022 and propagate to the image planes of the detectors.

Figure 12:
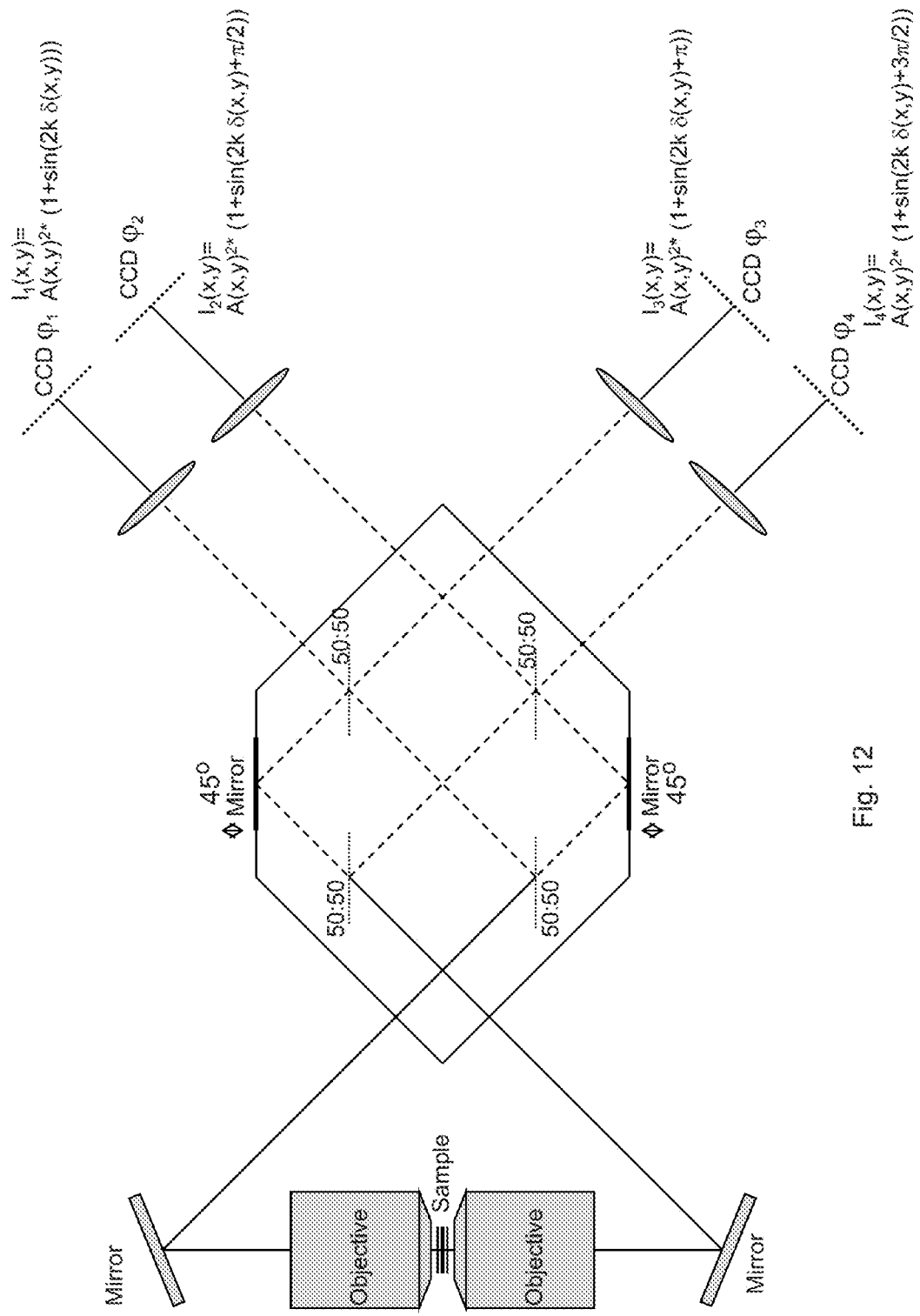
FIG. 12 shows a system block diagram of a four-phase interferometric microscope system, according to an embodiment of the invention.
Figure 13:
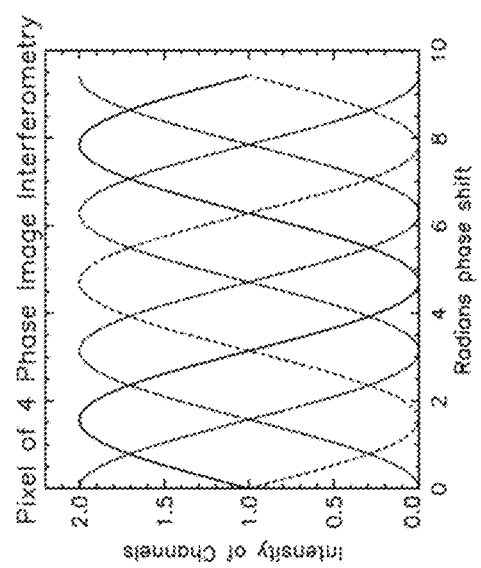
FIG. 13 shows a graph of the intensities of the radiated light detected at the four detectors of FIG. 12.

FIG. 12 shows a system block diagram of a four-phase interferometric microscopy system, according to an embodiment of the invention. FIG. 13 shows a graph of the intensities of the radiated light detected at the four detectors of FIG. 12. Although FIGS. 8 through 12 show embodiments having three- or four-phase interferometric microscopy systems, systems having more than four phases are possible such as five-phase interferometric microscopy systems, six-phases interferometric microscopy systems, etc.

Figure 8A:
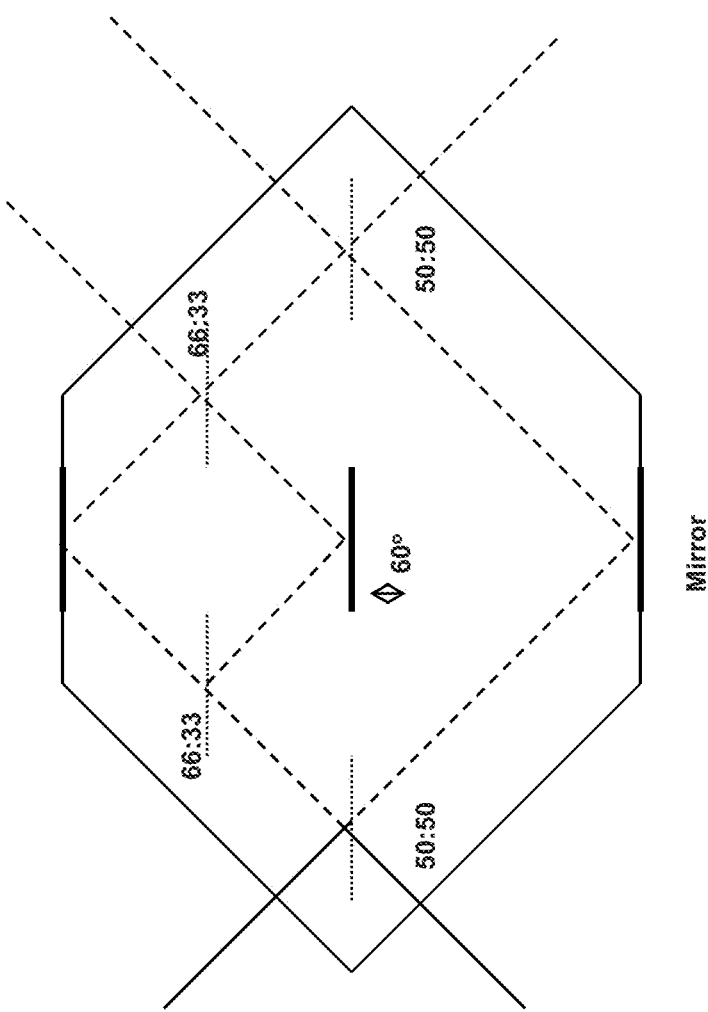
FIG. 8A shows a system block diagram of a three-way beam splitter, according to an embodiment of the invention.

While a two-phase interferometric microscopy system can use, for example, a beam splitter such as 50:50 beam splitter 250 as shown FIG. 2, the beam splitter for microscopy systems having more than two phases (e.g., as shown in FIG. 8) can be embodied in a number of different ways. For example, as shown in FIG. 8, the beam splitter can include multiple components: two 50:50 beam splitters, a 66:33 beam splitter and a mirror. These beam splitter components can be positioned manually, for example, on an optical bench. Alternatively, these beam splitter components can be manufactured and disposed between a pair of optical flats; the position of such beam splitter components can be adjusted, for example, by piezoelectric transducers. Such adjustments can insure that the phase shifts of the three legs are spaced by $2\pi/3$ or for a N leg embodiment by $2\pi/N$ and also parallelness of the splitting planes is established. An alternative embodiment of a 3-way beam splitter is shown in FIG. 8A.

Figure 8B:
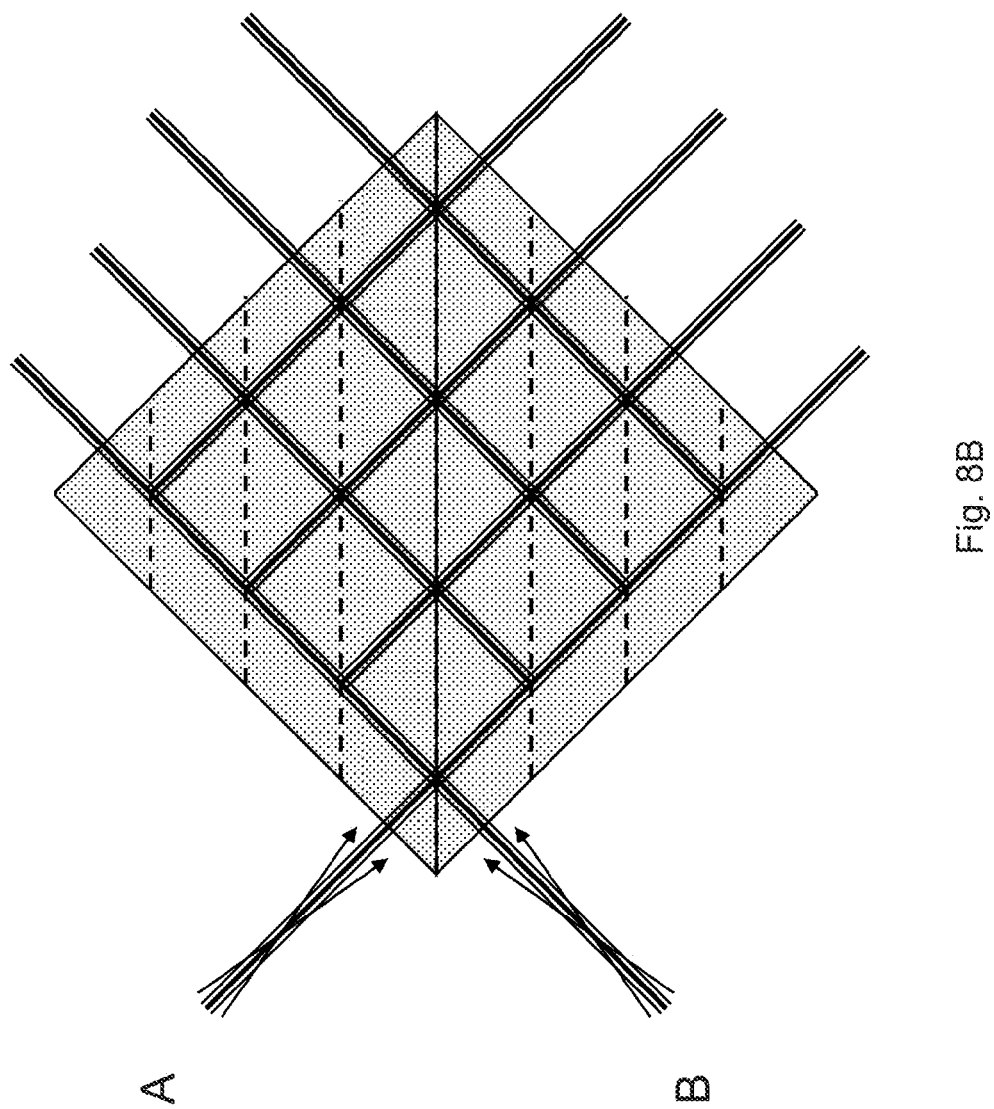
FIG. 8B shows a system block diagram of a eight-way beam splitter, according to yet another embodiment of the invention.

FIG. 8B shows a system block diagram of a eight-way beam splitter, according to yet another embodiment of the invention. As shown in FIG. 8B, the beam splitter includes multiple beam splitter components each of which is represented by a dashed line. Although FIG. 8B explicitly shows a beam splitter with 16 beam splitter components that produces 8 output beams, it should be understood that the basic structure can be followed for a greater or lesser number of beam splitter components to produce N number of output beams. These beam splitter components can have a reflectivity that ranges between 0 to 100%. Transmission can be nominal. When the surfaces of the beam splitter components are substantially parallel to each other, substantially the whole extent of a beam (or beam portion) (having a diameter, D) can interfere coherently with reflected beam portions of or other beam portions split from the original input beams A and B. The surfaces of the beam splitter components can be substantially parallel, for example, with each being within an angle of $<\lambda/D$. Also the beam splitter components are equally spaced to within a coherence length $\lambda^2/(n\Delta\lambda)$ of the input beams, where is wavelength, $\Delta\lambda$ is a range of wavelengths, and n is the index of refraction of the medium. This spacing insures that the interference is substantially coherent across the beam wavelength range dl of interest. Input beams A and B enter the beam splitter with a direction vector so that A-B is a vector normal to the planes of the beam splitter. Both input beams are aimed to the same point on the first beam splitter component. The parallel planar structure of the beam splitter allows a range of beams angles to self interfere; this range of beam angles can correspond to the range of angles associated with an image in a collimated portion of a beam before it is focused onto an image plane of, for example say a CCD detector (not shown in FIG. 8B). In some embodiments, both the reflectivity of each beam splitter component and the fine spacing between beam splitter components (less than the coherence length but enough to control interference angle) can be varied to ensure a substantially equal splitting into the N output beams (FIG. 8B shows N=8) for the case where only one input beam (e.g., input beam A or input beam B) is applied. Furthermore, in some embodiments, the interference angle between the input beam A and the input beam B can be set to different intervals of 360 degrees/N. So, in the example shown in FIG. 8B where N=8, the intervals of 45 degrees, 90 degrees, 135.degrees can be established.

Figure 14:
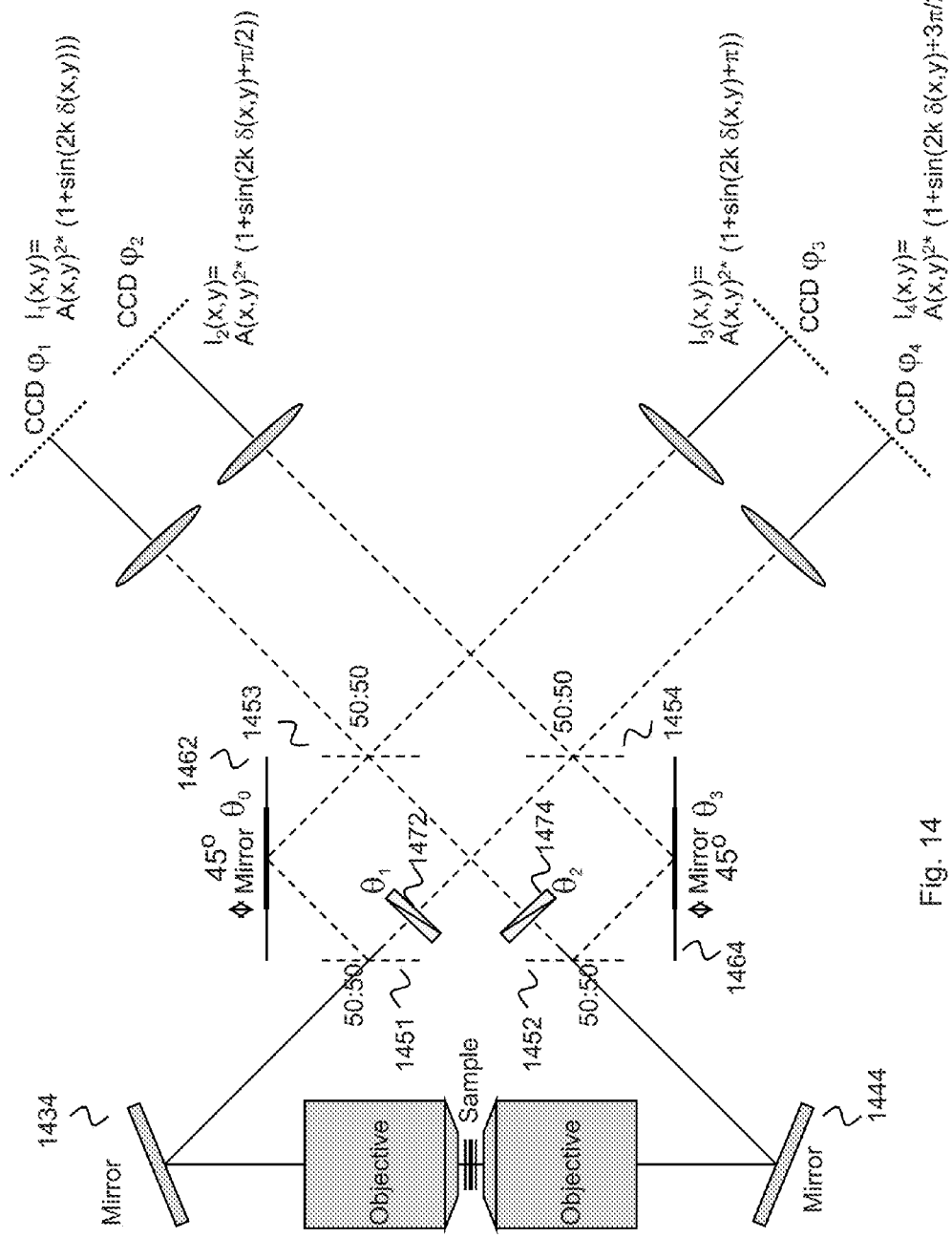
FIG. 14 shows a system block diagram of a four-phase interferometric microscope system having diffractive gratings, according to an embodiment of the invention.
Figure 15:
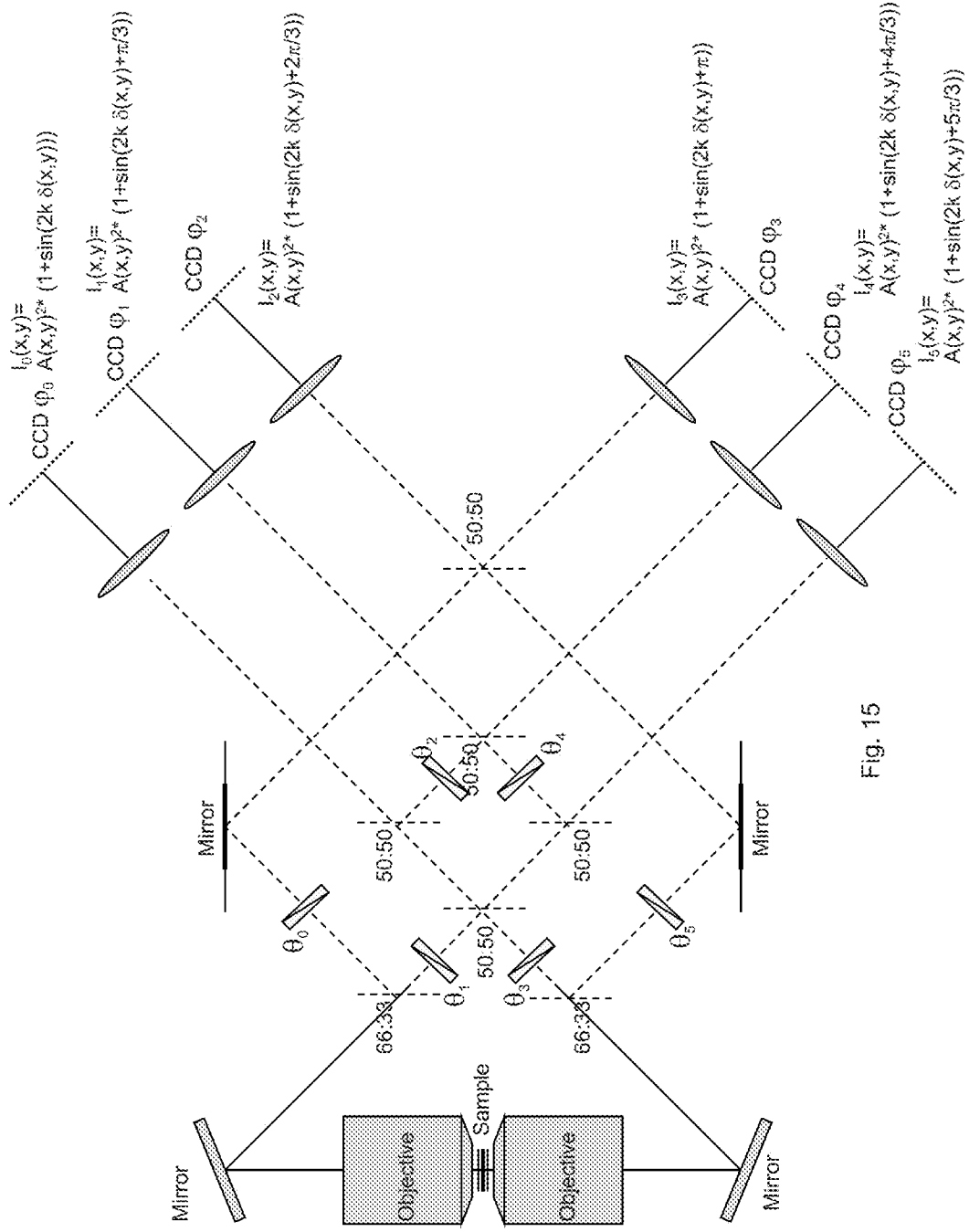
FIG. 15 shows a system block diagram of a six-phase interferometric microscope system having diffractive gratings, according to an embodiment of the invention.

As mentioned above, in some embodiments, one or more beam splitters can be based on diffraction gratings instead of beam splitters having thin-film coatings. For example, FIG. 14 shows a system block diagram of a four-phase interferometric microscope system having diffractive gratings, according to an embodiment of the invention. In this embodiment, the beam splitter 1450 includes diffraction gratings 1451 through 1454, mirrors 1462 and 1464, and phase shifters 1472 and 1474. Diffraction gratings 1451 and 1452 receive optical energy from mirrors 1434 and 1444, respectively. Diffraction grating 1451 divides the received optical energy and sends the divided portions to mirror 1462 and phase shifter 1472. Diffraction grating 1452 divides the received optical energy and sends the divided portions it to mirror 1464 and phase shifter 1472. Diffraction grating 1453 receives and mixes the optical energy from mirror 1462 and phase shifter 1474, divides the mixed optical energy, and sends each of the divided portions to a different detector. Similarly, diffraction grating 1454 receives and mixes the optical energy from mirror 1464 and phase shifter 1472, divides the mixed optical energy, and sends each of the divided portions to a different detector. FIG. 15 shows a system block diagram of a six-phase interferometric microscope system having diffractive gratings, according to another embodiment.

In some embodiments, spectral filters (e.g., bandwidth filters, low-pass filters or high-pass filters) can be disposed in the optical paths to reduce or prevent particular optical energies from contributing to the optical energy emitted from the switchable optical source. For example, optical energy used during photo-activation and/or photo-excitation can be removed from the optical paths to decrease stray light and noise within the optical paths and propagating towards the detectors.

In some embodiments, one or more the sample, objectives, mirrors, optical components, beam splitters, lenses, spectral filters and other elements along the optical paths can be coupled individually to multi-axis positioners including, for example, piezoelectric actuators. Such multi-axis positioners can allow for automated or non-automated calibration and positioning. Additionally, such multi-axis positioners can improve precision and accuracy in positioning and calibration over manual methods.

During setup and as a guide to positioning and alignment of the interferometer system, it can be useful to have a shutter incorporated into the two input beam paths. This allows one to observe the image from each path independently, and make sure that each path is optimally focused. Furthermore, because the images of the two portions can be observed, it is possible to shift one image with respect to the other so that they overlayed for optimal interference when the shutters are open for both beams.

In alternative embodiments having more than two-phases, the sensitivity can be phase invariant. In addition, the unique range of operation can be extended to $\lambda/2$. Larger displacements will result in a positional ambiguity modulo $\lambda/2$. This can be lifted with supplemental techniques, such as, for example, selective illumination (excitation or activation) in both space and time domain, or sample sectioning. In such embodiments, for example, having three-phase or four-phase interferometry, the position of the measured portion of the sample is determined by the intensities:

$$I_{ij}=G_j*(A_{Ui}^2+A_{Li}^2+2*\beta_j*A_{Ui}*A_{Li}*\cos(\phi_i+\phi_j))+Ofs_j)$$

where $j=0, 1, 2, \ldots$ indicates the leg of multiphase interferometer;
$I_j$=intensity of the j leg of point source, with offset no correction;
$\beta_j$=interference correction factor of $j^{th}$ leg;
$G_j$=gain of the $j^{th}$ leg;
$Ofs_j$=offset of the $j^{th}$ leg;
$A_{Ui}$=Amplitude of $i^{th}$ point source upper objective;
$A_{Li}$=Amplitude of $i^{th}$ point source lower objective;
$\phi_j$=$j^{th}$ leg phase shift; and
$\phi_i$=point source (i.e., fluorescent molecule) phase.

Dark calibration $A_{Ui}=A_{Li}=0$ allows one to determine the dark signal from the $j^{th}$ detector $$I_{oj}=G_j*Ofs_j$$

$$I_{ij}=G_j*(A_{Ui}^2+A_{Li}^2+2*\beta_j*A_{Ui}*A_{Ui}*\cos(\phi_i+\phi_j))+Ofs_j)$$
Total amplitude: $A_{Ti}^2=A_{Ui}^2+A_{Li}^2$ Rescaled interfering fraction:

$$X_i=2*A_{Ui}*A_{Li}/A_{Ti}^2$$

So, with these variables the intensities are:

$$I_{ij}=I_{oj}+G_j*A_{Ti}^2(1+\beta_j*X_i*\cos(\phi_i+\phi_j))$$

In alternative embodiments having more than two-phases, the sensitivity can be phase invariant. In addition, the unique range of operation can be extended to $\lambda/2$. Larger displacements will result in a positional ambiguity modulo $\lambda/2$. This can be lifted with supplemental techniques, such as, for example, selective illumination (excitation or activation) in both space and time domain, or sample sectioning. In such embodiments, for example, having three-phase or four-phase interferometry, the position of the measured portion of the sample is determined by the intensities:

$$I_{ij}=G_j*(A_{Ui}^2+A_{Li}^2+2*\beta_j*A_{Ui}*A_{Ui}*\cos(\phi_i+\phi_j))+Ofs_j)$$

where $j=0, 1, 2, \ldots$ indicates the leg of multiphase interferometer;
$I_j$=intensity of the j leg of point source, with offset no correction;
$\beta_j$=interference correction factor of $j^{th}$ leg;
$G_j$=gain of the $j^{th}$ leg;
$Ofs_j$=offset of the $j^{th}$ leg;
$A_{Ui}$=Amplitude of $i^{th}$ point source upper objective;
$A_{Li}$=Amplitude of $i^{th}$ point source lower objective;
$\phi_j$ leg phase shift; and
$\phi_i$=point source (i.e., fluorescent molecule) phase.

Dark calibration $A_{Ui}=A_{Li}=0$ allows one to determine the dark signal from the $j^{th}$ detector $$I_{oj}=G_j*Ofs_j$$

$$I_{ij}=G_j*(A_{Ui}^2+A_{Li}^2+2*\beta_j*A_{Ui}*A_{Li}*\cos(\phi_i+\phi_j))+Ofs_j)$$
Total amplitude: $A_{Ti}^2 A_{Ui}^2+A_{Li}^2$ Rescaled interfering fraction:

$$X_i=2*A_{Ui}*A_{Li}/A_{Ti}^2$$

So, with these variables the intensities are:

$$I_{ij}=I_{oj}+G_j*A_{Ti}^2(1+\beta_j*X_i*\cos(\phi_i+\phi_j))$$

A calibration where a fiducial source is moved by $\delta$ along z can be used to determine the remaining apparatus parameters $G_j$, $\beta_j$, and $\phi_j$. This will result in an intensity signal that oscillates in each leg similar to FIG. 7 for the three phase case as the phase $\phi_j(z) \sim 4*\pi/(n\lambda)\delta(z)$ winds. Here, n is the index of media with the shifted path length (e.g., immersion oil).

A fit to set of such calibration data will then determine the following equation for each leg j on a reference fiducial with interference fraction of the emitting fiducial $X_f$ and its intensity $A_{Tj}^2=I_f$ where the apparatus parameters $G_j$, $\beta_j$, and $\phi_j$ are now determined Such calibration can be useful in the phase-shift values are no exactly 120 degrees (3 legs) or $2\pi/N$ (N legs).

$$I_{fj}(z)=I_{oj}+G_j*I_f(1+\beta_j*X_f*\cos(\phi_j(z)+\phi_j)).$$

$G_j$, $\beta_j$ can be defined by normalizing to fiducial units:

$$I_f=1 \text{ and } X_f=1 \text{ and } \alpha_i=A_{Ti}^2/I_f$$

$$I_{ij}=I_{oj}+G_j*A_{Ti}^2(1+*X_1*\cos(\phi_i+\phi_j))$$

$$D_{ij}=(I_{ij}-I_{oj})/(G_j*I_f) \text{ rescaled intensity data}$$

$$D_{ij}=\alpha_i*(1+\beta_j*X_i*\cos(\phi_i+\phi_j))$$

Figure 26:
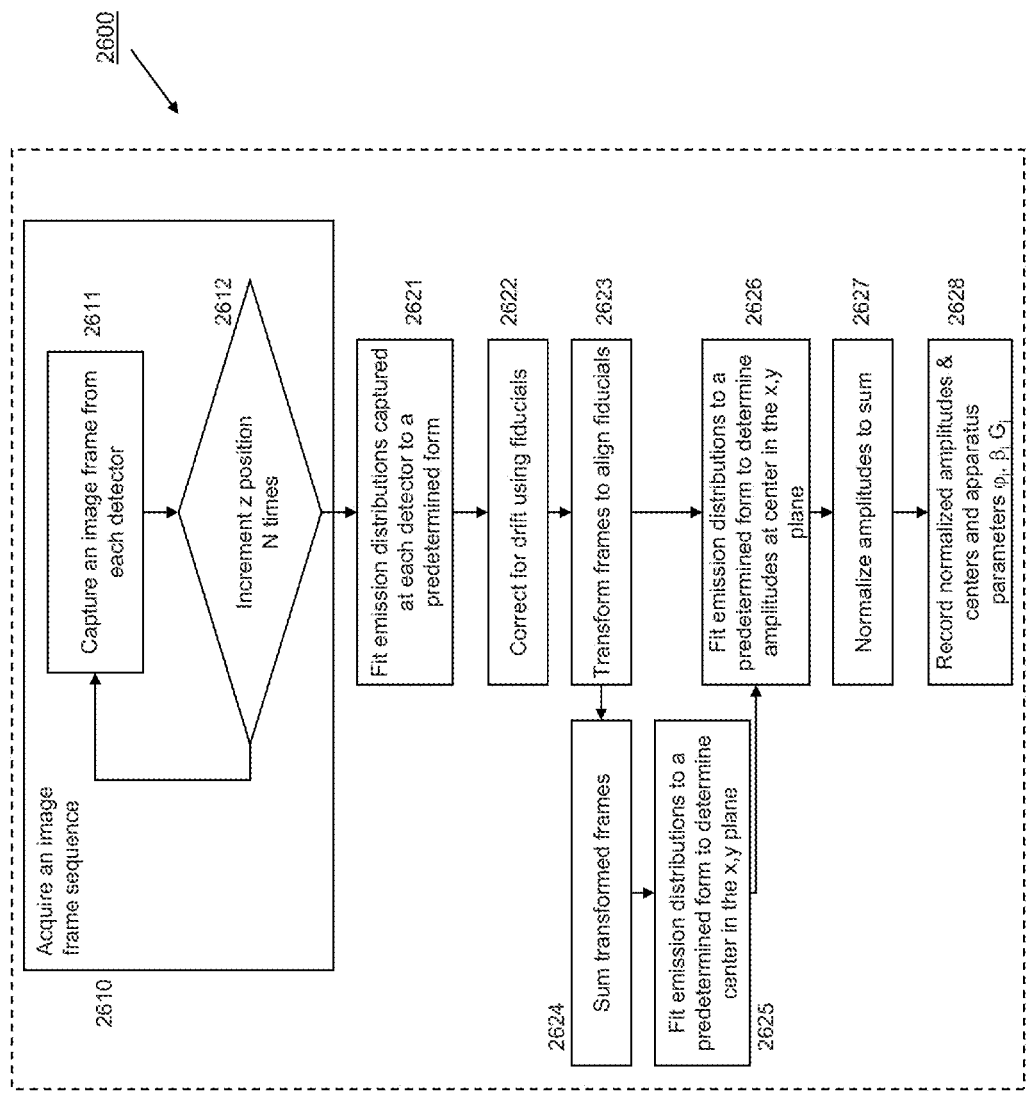
FIG. 26 shows a flowchart of a calibration process for a multi-phase interferometric microscope system, according to an embodiment of the invention.

FIG. 26 shows a flowchart of a calibration process 2600 for a multi-phase interferometric microscope system using an automated calibration method, according to an embodiment of the invention. At 2610, an optical emitter including sub-diffractive fiducials is imaged at various positions in the z plane to produce an image frame sequence. This process at 2610 includes sub-processes 2611 and 2612, which are repeatedly performed for various positions in the z plane to produce the image frame sequence. At 2611, an image of the optical emitter is captured at each detector in the interferometric microscope system. The image frames captured at each detector contain phase-related characteristics (e.g., $\phi_j$ $\beta_j$ of the $j^{th}$ detectors) that are phase-shifted relative to the information in the image frames captured at the other detectors. The z position of the optical emitter is incremented at 2612 and 2611 is repeated N times to produce an image frame sequence. Each image frame in an image frame sequence is based on optical energy intensities in the x,y plane relating to the emission distribution of the optical emitter.

At 2621, the emission distributions of the optical emitter are fit to a predetermined distribution to localize the optical emitter emission distribution in the x,y plane. For example, certain optical emitters have emission distributions that can be accurately fit to Gaussian distributions. Such Gaussian distributions can represent, for example, a likelihood a point spread function of the images of optical emitters. At 2622, the image frames are corrected for drift using the fiducials included in the image frames. The drift-corrected frames are then transformed at 2623 to produce transformed frame that align the fiducials in the image frames in the x,y plane.

At 2624, the image frames captured at each of the image detectors for each position in the z plane are summed into summed image frames. The summed image frames are a composite of the phase-shifted image frames captured by each detector. At 2625, the summed image frames are fit to a predetermined distribution to determine the center of the optical emitter in the x,y plane.

The transformed frames are fit at 2626 to a predetermined distribution, such as a Gaussian distribution, and the amplitude of the optical emitter emission distribution in each frame is measured at the center of the optical emitter in the x,y plane determined in 2625. The center of the optical emitter can be based on, for example, the centroid of a Gaussian distribution (e.g., a three-dimensional distribution) representing a likelihood of the location of an optical emitter. At 2627, the amplitudes of the optical emitter emission distribution are normalized to the sum determined at 2624. The normalized amplitudes determined at 2627 for each image and the associated z position is recorded at 2628. For example, the normalized amplitudes and the associated z positions for each frame can be stored within a look-up table or parameterized by the previous equations to determine $\phi_j$ and $\beta_j$.

The following equations set forth an explanation by which the displacement, $\delta$, of source (i.e., the relative z-coordinate position of the sample) can be determined from the intensity data collected by the interferometry microscopy system.

Once the calibration is complete, the data can be scaled and then the values $\beta_j$ and $\phi_j$ are also known for each output beam of the interferometer. The j equations:

$$D_{ij}=\alpha_i*(1+\beta_j*X_i*\cos(\phi_i(z)+\phi_j))$$

can be used to determine the position of an emitter along the axial direction. Thus three or more data values $D_{i0}$, $D_{i1}$, $D_{i2}$, ... for the intensity of the $i^{th}$ molecule result in three or more equations to determine the three unknown values: $\alpha_i$, $X_i$, and (of most interest) $\phi_i(z)$. If there are only three phases, then the three equations will yield a unique solution for these three unknowns. This and the value of $\phi_i$ in particular can be solved for example by Newton's Method.

If there are more than three phases, then four or more equations can determine the three unknown values and the system of equations is over constrained. In that case, the best values for the unknowns can be determined using a chi-squared minimization method. By minimizing the error of the equations:

$$\chi_i=\Sigma_j[D_{ij}-\alpha_i(1+\beta_j\cos(\phi_i+\phi_j))]^2$$

In the approximation of a well balanced interferometer system (meaning phase shift increment between cameras and equalized gain and equalized interference efficiency) we can obtain a best value for $\phi_i$ given by the equation:

$$\tan(\phi_i)\cong-\Sigma_j D_{ij}\sin(\phi_j)/\Sigma_j D_{ij}\cos(\phi_j)$$

Once the phase $\phi_i$ of the $i^{th}$ emitter is known then the vertical position $\delta_i$ along the z axis can be deduced to a first approximation by the equation. Note n is the index of refraction of the sample environment.

$$\delta_i\cong\lambda*\phi_i/(4\pi n)=\lambda/(4\pi n)*a\tan(\Sigma_j D_{ij}\sin(\phi_j)/\Sigma_j D_{ij}\cos(\phi_j))$$

This last equation solving for displacement, $\delta$, describes the phase shift from the intensity data. In other words, this last equation shows how the displacement, $\delta$, can be calculated based on the intensity data detected at the detector for each leg of the interferometry microscope system. For example, for a 3-phase interferometry microscope system $(\phi_j)\cong-2\pi/3, 0, 2\pi/3$. For a 4-phase interferometry microscope, $(\phi_j)\cong 0, \pi/2, \pi, 3\pi/2$.

Note that the above equation for calculating displacement, $\delta$, is based on various assumptions. In alternative embodiments, other assumptions can be used resulting in one or more alternatives for calculating the displacement, $\delta$. For example, higher order corrections can be calculated from the real part and taking out the approximations that the N phases of each interferometer leg are equally spaced or that the sensitivity of interferometer leg is equal. Alternative embodiments can include further refinements that provide a means to calibrate and correct for non-balanced intensity sensitivities and phase mixing angles.

In summary, the N spot intensities of a N phase interferometer becomes the data $D_j$ that can be converted to the vertical position displacement $\delta$.

Because $\phi_i$ is a cyclic solution, for every $2\pi$ the uniquely determinable range extends $\lambda/2n$. For samples thicker than this, an ambiguity exists in determining $\delta$ by +/−N $\lambda/2n$ for an integer N. Other attributes, such as measured point spread function and interference efficiency, can be used to find the most likely N and chose the best of a multi-valued solution. In effect the extent of defocus is an alternate, less precise but adequate method to estimate to within $\lambda/2n$ where the emitter is located. This combined with the interferometricly-deduced position can give a unique vertical position of the emitter. One further consideration in estimating the vertical position is to account for the Gouy phase, an extra term that advances the phase by an extra π at the focus over about a Rayleigh length distance $z_R$. In this case δ is given by the solving the following equation:

$$\phi_i \cong (4\pi\delta/(n\lambda)) + a \tan(\delta/z_R).$$

Figure 27:
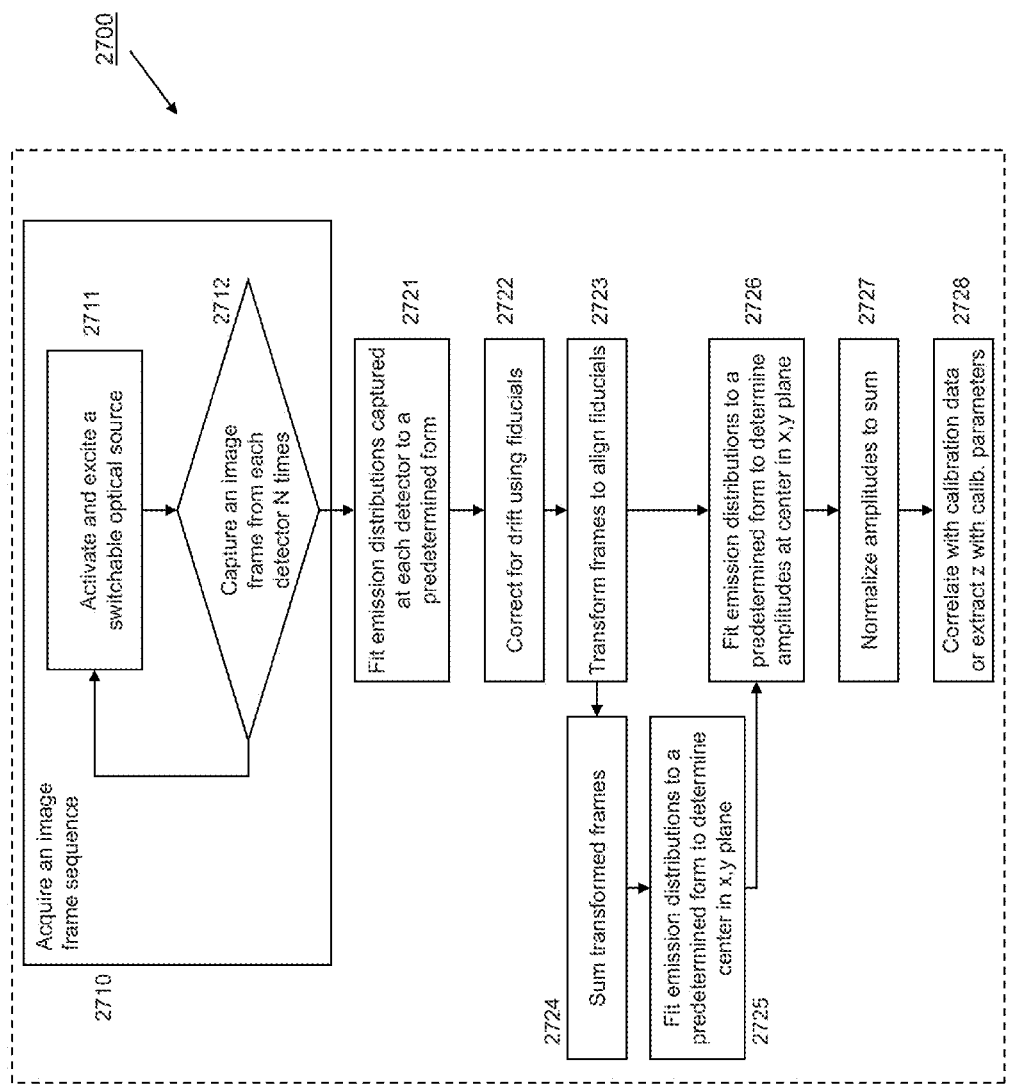
FIG. 27 shows a flowchart of a process for obtaining 3-dimensional position information of photo-activated samples within a multi-phase interferometric microscope system, according to an embodiment of the invention.

FIG. 27 shows a flow chart of a process for obtaining 3-dimensional position information of photo-activated samples within a multi-phase interferometric microscope system, according to an embodiment of the invention. At 2710, various switchable optical sources including sub-diffractive fiducials are imaged to produce an image frame sequence. This process at 2710 includes sub-processes 2711 and 2712, which are repeatedly performed for various positions in the z plane to produce the image frame sequence. At 2711, a switchable optical source is activated and excited. At 2712, an image frame is captured at each detector in the interferometric microscope system and 2711 is repeated N times to produce an image frame sequence. The image frames captured at each detector contain phase-related characteristics that are phase-shifted relative to the information in the image frames captured at the other detectors. The image frames are based on optical energy intensities in the x,y plane relating to the emission distributions of the switchable optical sources.

At 2721, the emission distributions of the switchable optical sources are fit to a predetermined distribution to localize the emission distributions of the switchable optical sources in the x,y plane. For example, certain switchable optical sources have emission distributions that can be accurately fit to Gaussian distributions. Such Gaussian distributions can represent, for example, a point spread function of the images of optical emitters. At 2722, the image frames are corrected for drift using the fiducials included in the image frames. The drift-corrected frames are then transformed at 2723 to produce transformed frames that align the fiducials in the image frames of the image frame sequence in the x,y plane.

At 2724, the image frames captured at each of the image detectors for each position in the z plane are summed into summed image frames. The summed image frames are a composite of the phase-shifted image frames captured by each detector. At 2725, the summed image frames are fit to a predetermined distribution to determine the centers of the switchable optical sources in the x,y plane.

The transformed frames are fit at 2726 to a predetermined distribution, such as a Gaussian distribution, and the amplitude of the emission distribution of the switchable optical source in each frame is measured at the centers of the switchable optical sources in the x,y plane determined in 2725. The center of the optical emitter can be based on, for example, the centroid of a Gaussian distribution representing a likelihood of the location of an optical emitter. At 2727, the amplitudes of the emission dispersions of the switchable optical source are normalized to the sum determined at 2724. At 2728, the normalized amplitudes determined at 2727 are used to obtain the z plane coordinate of the switchable optical source by correlation with calibration data recorded at previous step 2528. Such calibration data can be stored, for example, in a lookup table. The z plane coordinated can be calculated based on the normalized amplitudes, for example, by determining the minimum chi-square of:

$$[CA_1(z)-PA_1]^2+[CA_2(z)-PA_2]^2+[CA_3(z)-PA_3]^2+\ldots+[CA_N(z)-PA_N]^2$$

where N=the number of detectors in the system;
$CA_i(z)$=the normalized peak optical energy intensity amplitude at detector $_i$ determined during calibration for a particular sample position in the z plane;
$PA_i$=normalized peak optical energy intensity amplitude at detector determined from the current PALM image frame.

Figure 16:
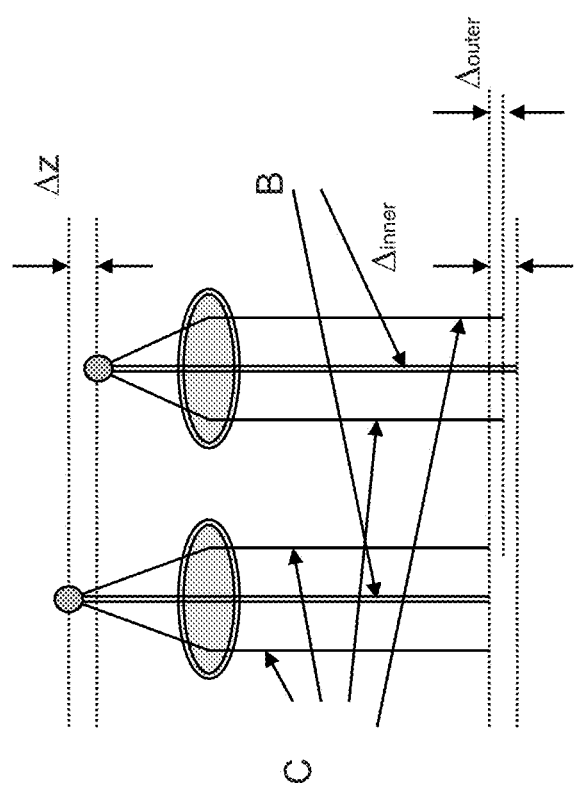
FIG. 16 shows a diagram of a single quantum emitter in two different potential locations.
Figure 17:
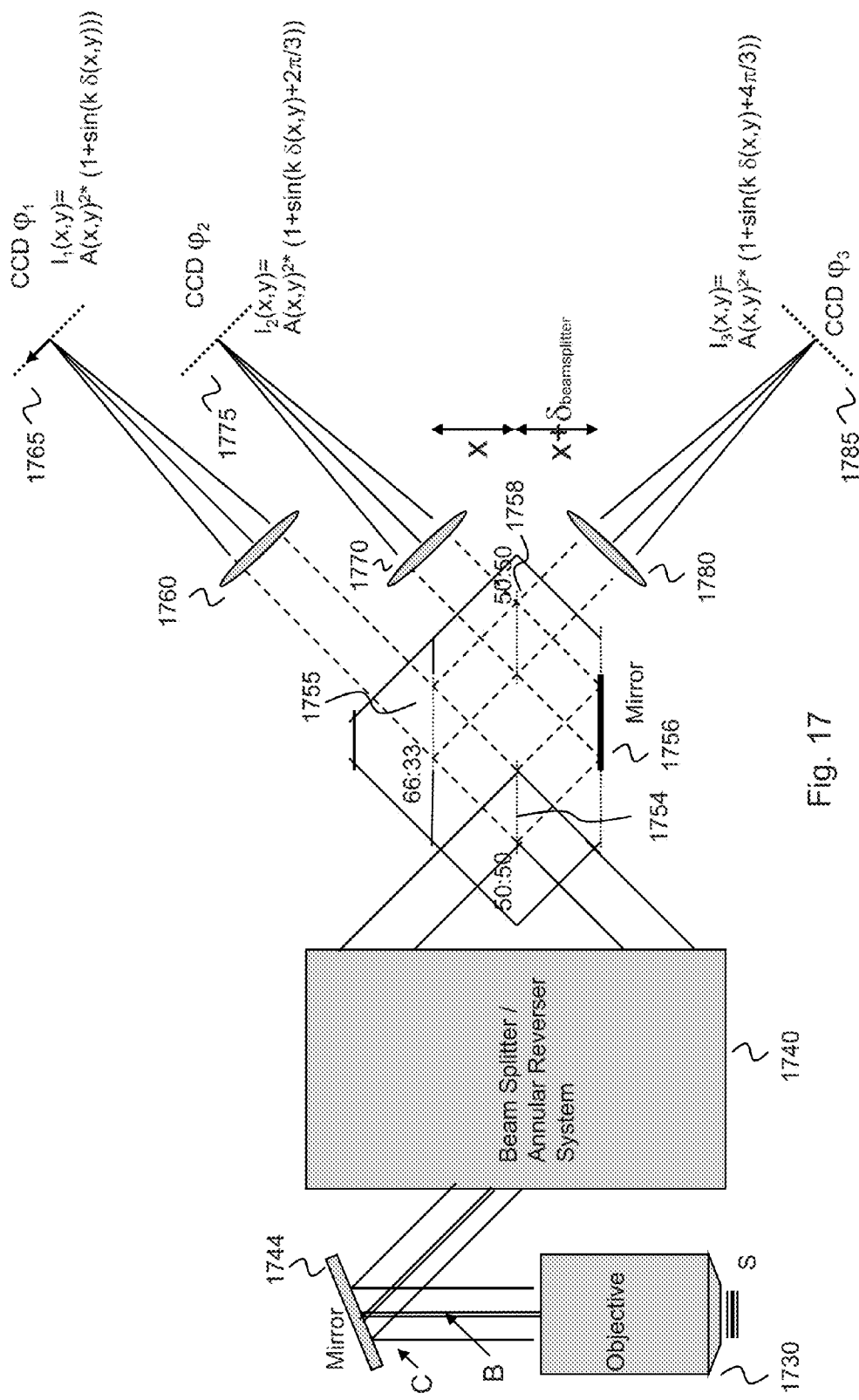
FIG. 17 shows a system block diagram of a three-phase interferometric microscopy system having a single objective, according an embodiment of the invention.
Figure 18:
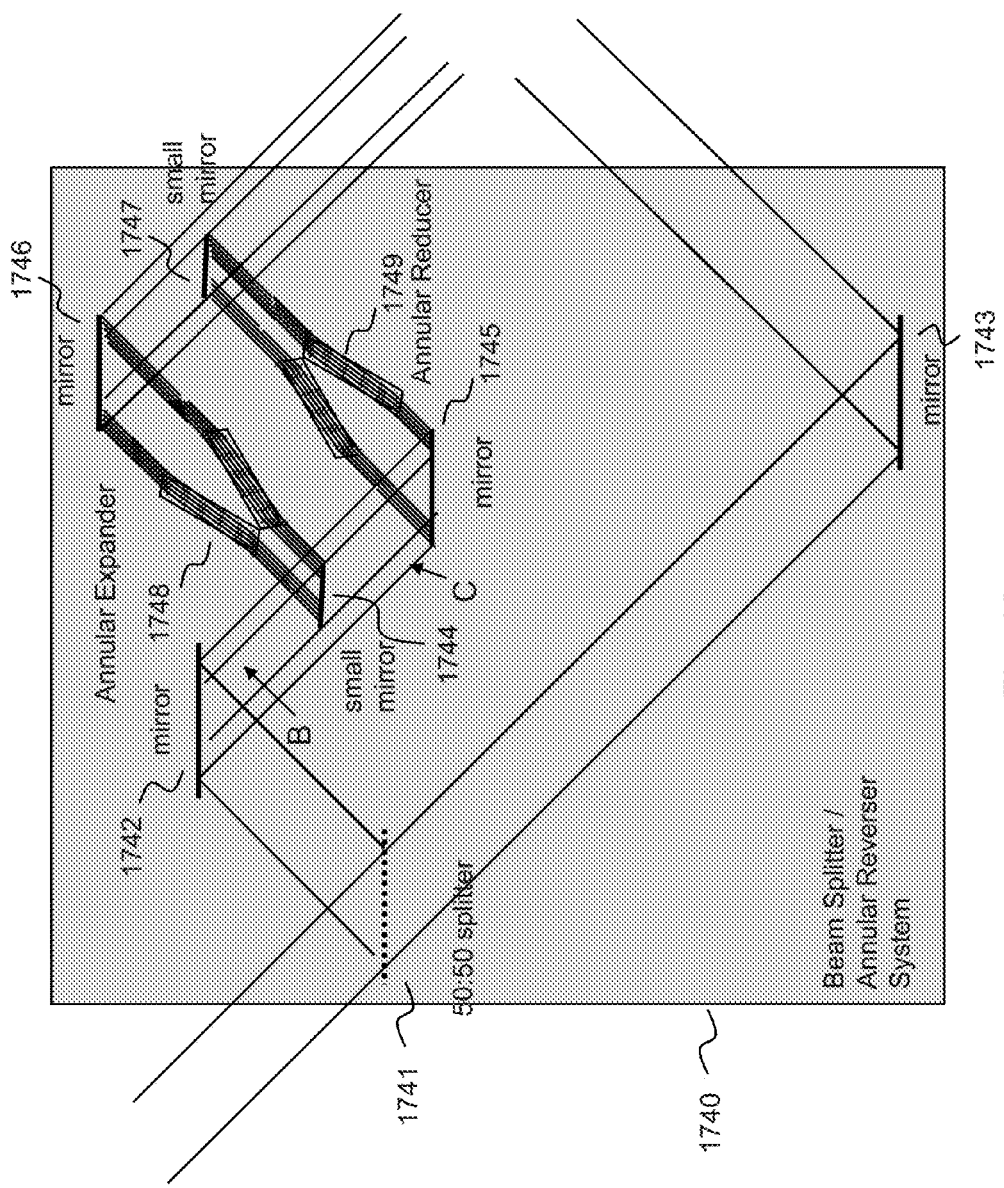
FIG. 18 shows an example of a system block diagram of the beam splitter/annular reverser system shown in FIG. 17.
Figure 20:
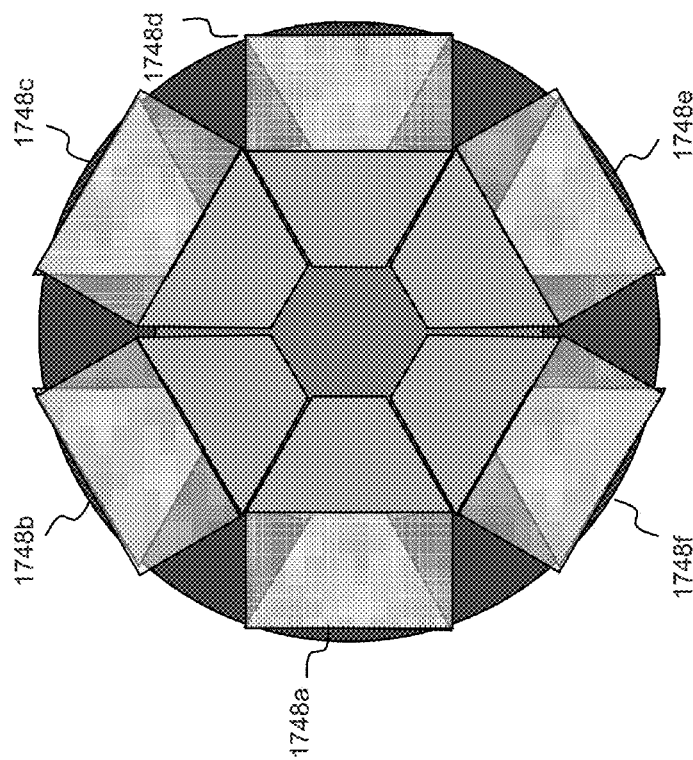
FIG. 20 shows an end view of the annular expander shown in FIG. 18.
Figure 19:
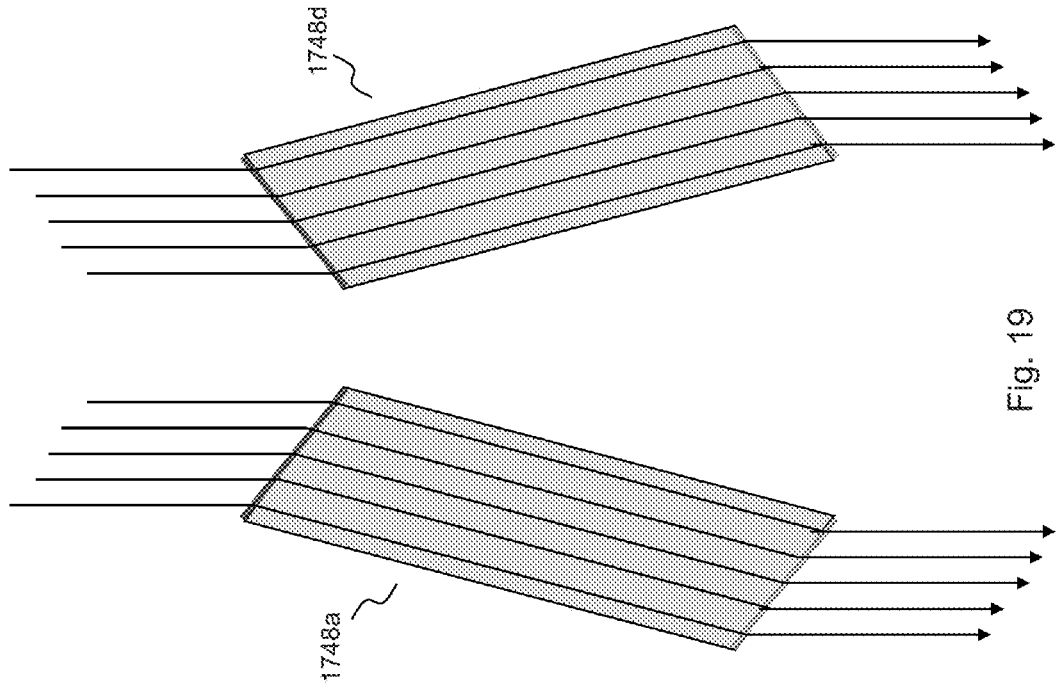
FIG. 19 shows a cross-sectional view of the annular expander shown in FIG. 18.
Figure 22:
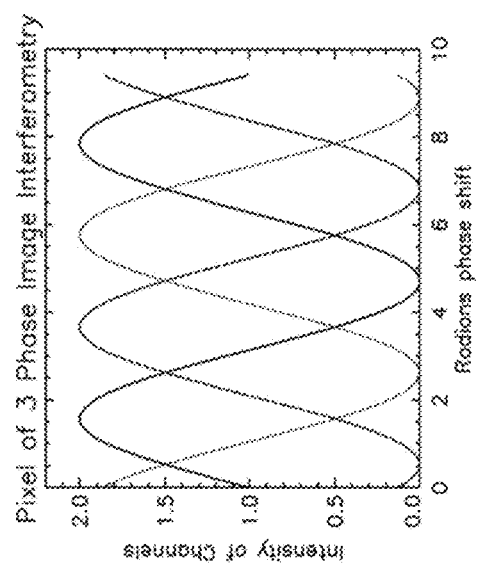
FIG. 22 shows a graph of the intensities of the radiated light detected at the three detectors of FIG. 17.

In another embodiment, an interferometric microscopy system can use different portions of the emitted beam that still generate a path length difference that varies with a third dimension z. Such an alternative embodiment is discussed in connection with FIGS. 16-22. More specifically, FIG. 16 shows a diagram of a single quantum emitter in two different potential locations; FIGS. 17 and 18 show an example of a system block diagram of a three-phase interferometric microscopy system having a single objective; FIGS. 19-21 show an example of an annular expander of FIG. 18; FIG. 22 shows a graph of the intensities of the radiated light detected at the three detectors of FIG. 17. These figures are discussed below.

FIG. 16 shows an example of a single quantum emitter, in two possible locations. Such a quantum emitter can be, for example, a fluorescent molecule, a quantum dot or a sub-wavelength scattering center. A radiated photon (wavelength 2) will propagate in all directions including an upward direction away from the objective shown in FIG. 17 and a downward direction into the objective shown in FIG. 17. The portion of the energy of the radiated photon propagating into the objective can be considered as two collimated beams of roughly equal strength: an inner cylindrical beam labeled "B" and an outer annular beam labeled "C." The size of inner beam portion B and outer beam portion C can be selected such that their intensities are substantially equal; such substantially equal intensities correspond to different beam portion areas due to the non-linear intensity profile of the beam (e.g., the peak of the beam energy is in the center of the beam with the intensity reducing towards the edges of the beam). For example, the inner beam portion labeled "B" can have a radius equal to approximately one third of the total beam radius; the outer beam portion labeled "C" can have an inner radius corresponding to the radius of the inner beam portion "B" and an outer radius corresponding to the radius of the total beam.

When the sample is exactly in focus, these beam portions are matched and in phase (as shown in the left side of FIG. 16). When, however, there is a positional displacement Δz of the emitter (as shown in the right side of FIG. 16), the phase beam portions B and C are displaced by $\Delta_{inner}$ and $\Delta_{outer}$, respectively, where $\Delta_{inner}$ equals Δz and $\Delta_{outer}$ equals Δz*cos(θ). This displacement of the phase beam portions B and C is due to the fact that the outer beam portion C will undergo less of an optical path change by a factor of cos(θ), where θ is the initial cone angle of rays from the emitter. Consequently, a differential phase shift between the two beams remains and equals:

$$\delta=2\pi(\Delta_{inner}-\Delta_{outer})/\lambda=\Delta z*(1-\cos(\theta))*2\pi n/(\lambda).$$

The z range over which the phase increases through 360 degrees and repeats is: λ/(n(1−cos(θ))). This z range for this single-objective embodiment is longer than the z range of the opposing-objective embodiments discussed above in connection with FIGS. 1-11. The index of refraction, n, of the optical environment around the emitter rescales the phase shift. An embodiment of a single-objective system is discussed in more detail below in connection with FIGS. 17-20.

FIG. 17 shows an example of a system block diagram of a three-phase interferometric microscopy system having a single objective. FIG. 18 shows an example of a system block diagram of the beam splitter/annular reverser system shown in FIG. 17. As shown in FIG. 17, the interferometric microscopy system includes an objective 1730; a mirror 1744; a beam splitter/annular reverser system 1740; mirror 1756; beam splitters 1754, 1755 and 1758; lens 1760, 1770 and 1780; and detectors 1765, 1775 and 1785. As shown in FIG. 18, the beam splitter/annular reverser system 1740 includes a beam splitter 1741, mirrors 1742-1747, annular expander 1748 and annular reducer 1749.

The annular expander 1748 can be any type of device that receives light having a given radius and expands the radius of the light. For example, the annular expander 1748 can receive the inner cylindrical beam of light from the mirror 1742 (similar in cross-sectional shape to the inner beam "B" discussed in reference to FIG. 17) and can produce light having an annular shape with a larger outer diameter (e.g., similar in cross-sectional shape to the outer beam "C" discussed in reference to FIG. 17). Similarly, annular reducer 1749 can be any type of device that receives light having a given radius and reduces the radius of light. For example, the annular reducer 1749 can receive the outer annular beam of light from the mirror 1742 (similar in cross-sectional shape to the outer beam "C" discussed in reference to FIG. 17) and can produce light having an inner cylindrical shape (or smaller annular shape) with a smaller inner diameter (e.g., similar in cross-sectional shape to the inner beam "B" discussed in reference to FIG. 17).

FIGS. 19-21 show an example of an annular expander shown in FIG. 18. More specifically, FIG. 19 shows a cross-sectional view of the annular expander shown in FIG. 18; FIG. 20 shows an end view of the annular expander shown in FIG. 18; and FIG. 21 shows a perspective view of three out of the six prism components of the annular expander shown in FIG. 18. As shown in FIGS. 19-21, the annular expander 1748 has six prisms 1748a-1748f spaced about a centerline of the annular expander 1748 such that one end of the six prisms 1748a-1748f collectively defines an annular-like, multi-faceted surface having a size different from the size of the annular-like, multi-facted surface collectively defined by the other end of the six prisms 1748a-1748f. The light enters the end of the prisms 1748a-1748f defining the smaller, annular-like, multi-faceted surface and exits the end of the prisms 1748a-1748f defining the larger, annular-like, multi-faceted surface, as shown in FIG. 19. FIG. 20 shows the end view of the annular expander 1748 from the larger, annular-like, multi-faceted surface towards the smaller, annular-like, multi-faceted surface into the page. Although not explicitly shown, the annular reducer 1749 would be configured similar to the annular expander 1748 except that light enters the end of the prisms defining the smaller, annular-like, multi-faceted surface and exits the end of the prisms defining the larger, annular-like, multi-faceted surface.

Returning the FIGS. 17 and 18, the three-phase interferometric microscopy system will now described with reference to light propagating through the system. As shown in FIG. 17, energy is radiated from the sample (labeled "S" in FIG. 17) and reflected by mirror 1744 to beam splitter/annular reverser system 1740. The 50:50 beam splitter 1741 of beam splitter/annular reverser system 1740 (shown in FIG. 17) sends a portion of the light to mirror 1742 and a remaining portion of the light to mirror 1743. To separate the light into two beam portions, the mirror 1742 reflects an outer beam portion C towards mirror 1745 while reflecting an inner beam portion beam B to mirror 1744. Mirrors 1745 and 1744 reflect outer beam portion C and inner beam portion B, respectively, to annular expander 1748 and annular reducer 1749, respectively. Annular expander 1748 expands its received light towards mirror 1746, which reflects the expanded light towards beam splitter 1754 (shown in FIG. 17). Similarly, annular reducer 1749 reduces the radius of its received light towards mirror 1747, which reflects the reduced light towards 50:50 beam splitter 1754.

50:50 beam splitter 1754 reflects half of the light received from mirrors 1746 and 1747 to 66:33 beam splitter 1755 and transmits the other half of the light to mirror 1756. 50:50 beam splitter 1754 also reflects half of the light received from mirror 1743 to mirror 1756 and transmits the other half of the light to 66:33 beam splitter 1755. The 66:33 beam splitter 1755 reflects 33% of the received beam towards 50:50 beam splitter 1758 and transmits the remaining 66% of the received beam towards lens 1760. Mirror 1756 reflects the received beam to 50:50 beam splitter 1758 while also adding an extra phase shift. The 50:50 beam splitter 1758 reflects 50% of the received beam from mirror 1756 towards lens 1780 and transmits 50% of the received beam from mirror 1756 towards lens 1770. The 50:50 beam splitter 1758 also reflects 50% of the received beam from the 66:33 beam splitter 1755 towards lens 1770 and transmits 50% of the received beam from the 66:33 beam splitter 1755 towards lens 1780.

Note that the 50:50 beam splitters 1754 and 1758, mirror 1756 and 66:33 beam splitter 1755 can be arranged such that a difference exists in the light path lengths. More specifically, the optical path distance, x, between the 50:50 beam splitters 1754 and 1758 and the 66:33 beam splitter 1755 can be less than the distance, $\lambda + \delta_{beamsplitter}$, between the 50:50 beam splitters 1754 and 1758 and the mirror 1756. Assuming, for example, that the optical path difference between the two distances, $\delta_{beamsplitter}$, can be selected to be ⅛ of the wavelength, $\lambda$, and the wavelength, $\lambda$, is 580 nm, the difference between the two distances, $\delta_{beamsplitter}$, can be selected at 72 nm.

The beam sent to lens 1760, the beam sent to lens 1770 and the beam sent to lens 1780 each have substantially equal amplitudes. Lenses 1760, 1770 and 1780 focus the respective beams to detectors 1765, 1775 and 1785, respectively. The intensity of the emitted image on each of the three detectors 1765, 1775 and 1785 changes as a function of the phase/z position because the relative intensities among the three detectors 1765, 1775 and 1785 have about a 120-degree phase shift. FIG. 22 shows a graph of the intensities of the radiated light detected at the three detectors shown in FIG. 17. By monitoring the intensities detected by the three detectors 1765, 1775 and 1785, the phase shift from the initial offset between the inner beam portion B and the outer beam portion C can be estimated as described above in connection with FIGS. 1-11.

This phase shift, $\delta$, can be used to calculate the z position of the emitter:

$$\Delta z = \delta \lambda / (n(1 - \cos(\theta))).$$

In some embodiments, calibration techniques can be used to correct for non-balanced intensity sensitivities of the detectors and phase mixing angles. Although the embodiments shown in FIGS. 17-22 are described with respect to three detectors having approximately 120-degree phase shifts, other embodiments having a different number of detectors are possible. In yet other embodiments, the imaged spot shape can be used to resolve any cyclic or positional ambiguity. Alternatively, the imaged spot shape can be used as additional information for the positional calculation.

Figure 23:
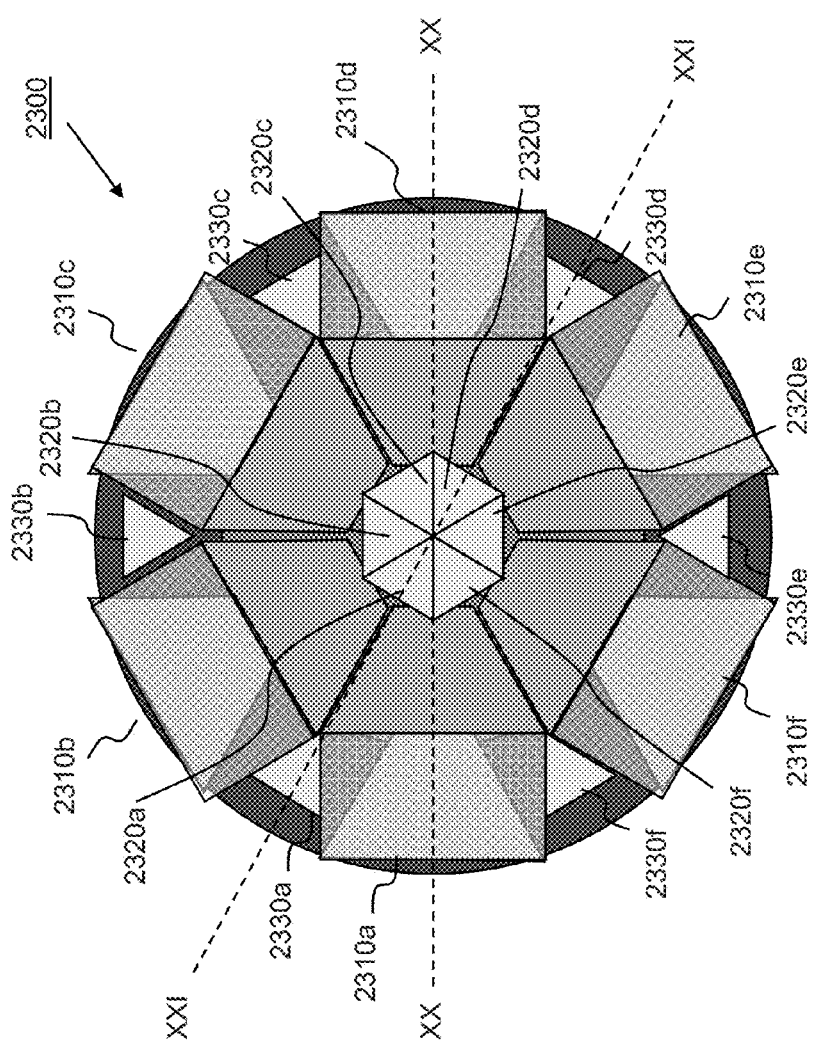
FIG. 23 shows an end view of the annular expander, according to another embodiment of the invention.
Figure 25:
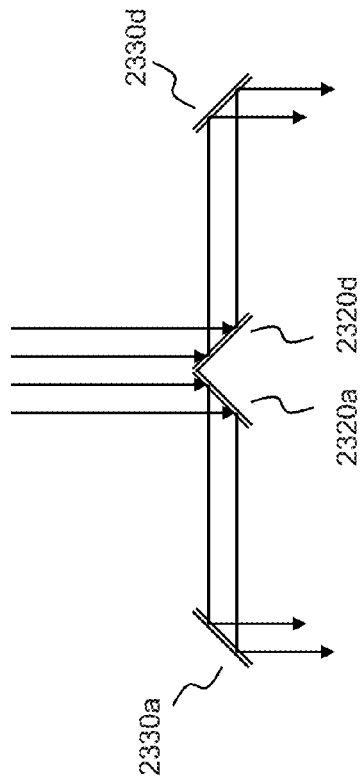
FIG. 25 shows a cross-sectional view of the annular expander shown in FIG. 23 along line XXI-XXI.
Figure 24:
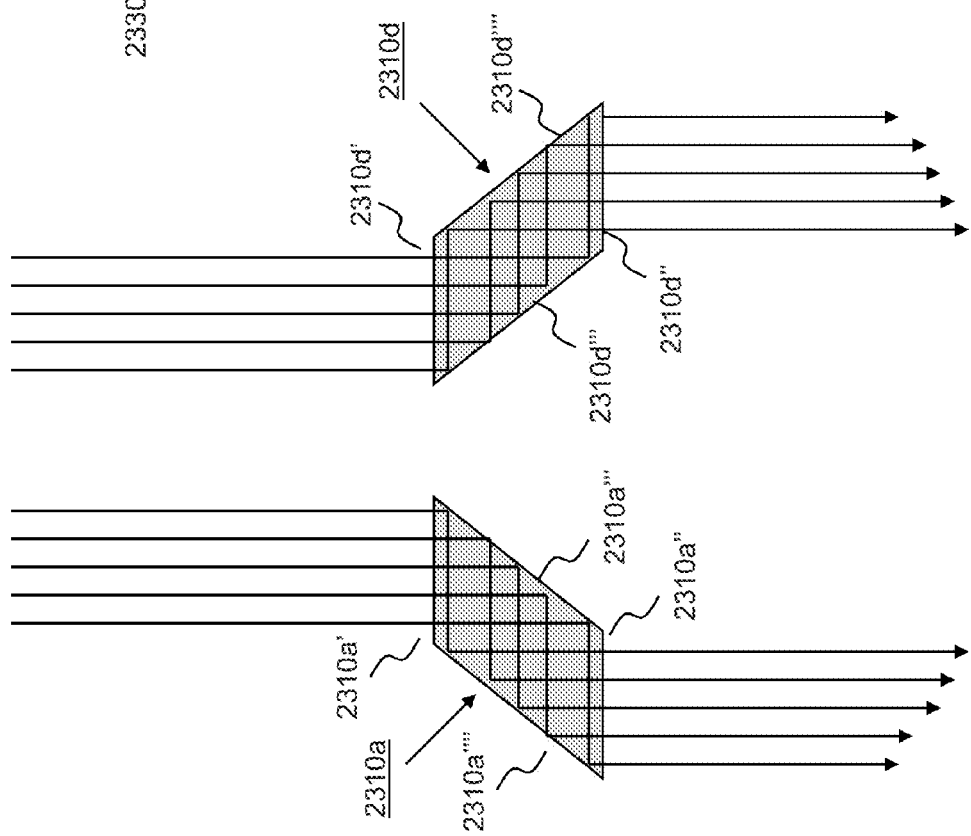
FIG. 24 shows a cross-sectional view of the annular expander shown in FIG. 23 along line XX-XX.

FIGS. 23-25 show an example of an annular expander, according to another embodiment of the invention. More specifically, FIG. 23 shows an end view of the annular expander; FIG. 24 shows a cross-sectional view of the annular expander of FIG. 23 along the line XX-XX; FIG. 25 shows a cross-sectional view of the annular expander of FIG. 23 along the line XXI-XXI. As shown in FIGS. 23-25, the annular expander 2300 has six prisms 2310a-2310f, six mirrors 2320a-2320f and six mirrors 2330a-2330f. The prisms 2310a-2310f are spaced about a centerline of annular expander 2300 such that one end of the six prisms collectively defines an annular-like surface having a size different from the size of the annular-like surface collectively defined by the other end of the six prisms. The mirrors 2320a-2320f are arranged about the centerline of annular expander 2300 and within an interior central portion defined by the six prisms 2310a-2310f. The mirrors 2330a-2330f are arranged about the centerline of annular expander 2300 and about an outer portion defined by the gaps between adjacent prisms 2310a-2310f.

As shown in FIG. 24, each prism 2310 includes an ingress face 2310' and an egress face 2310''. The ingress face 2310' is parallel to and has a smaller inner radius and outer radius than egress face 2310''. Each prism 2310 also includes two side walls 2310''' and 2310'''' angled relative to the ingress face 2310' and the egress face 2310'' such that the condition for total internal reflection (TIR) is satisfied. Thus, light enters each prism 2310 at the ingress face 2310', undergoes a reflection due to TIR at side wall 2310''' and a reflection due to TIR at side wall 2310', and then exits from the egress face 2310''. This allows the radius of the incident light to be expanded as it exits the annular expander 2300.

As shown in FIG. 25, the mirrors 2320a-2320f reflect the light along and near the centerline of annular expander 2300 outwardly towards mirrors 2330a-2330f, respectively. Mirrors 2330a-2330f reflect the received light between the gaps defined by adjacent prisms 2310a-2310f. For example, mirror 2320a reflects a portion of light near the centerline of annular expander 2300 towards mirror 2330a, which reflects this lights between the gap defined between prism 2310a and prisms 2310b. Collectively, this allows the central portion of the light to be expanded, providing increased throughput.

Although not explicitly shown, an annular reducer can be configured similar to the annular expander 2310 except that light enters the end of the prisms defining the larger, annular-like surface and exits the end of the prisms defining the smaller, annular-like surface. Although the embodiments shown in FIGS. 19-20 and 23-25 shown with specific refractive and/or reflective components, other embodiments and arrangements are possible including, for example, embodiments having diffractive components or any combination thereof.

Some embodiments include a processor and a related processor-readable medium having instructions or computer code thereon for performing various processor-implemented operations. Such processors can be implemented as hardware modules such as embedded microprocessors, microprocessors as part of a computer system, Application-Specific Integrated Circuits ("ASICs"), and Programmable Logic Devices ("PLDs"). Such processors can also be implemented as one or more software modules in programming languages as Java, C++, C, assembly, a hardware description language, or any other suitable programming language. A processor according to some embodiments includes media and computer code (also can be referred to as code) specially designed and constructed for the specific purpose or purposes. Examples of processor-readable media include, but are not limited to: magnetic storage media such as hard disks, floppy disks, and magnetic tape; optical storage media such as Compact Disc/Digital Video Discs ("CD/DVDs"), Compact Disc-Read Only Memories ("CD-ROMs"), and holographic devices; magneto-optical storage media such as floptical disks, and read-only memory ("ROM") and random-access memory ("RAM") devices. Examples of computer code include, but are not limited to, micro-code or micro-instructions, machine instructions, such as produced by a compiler, and files containing higher-level instructions that are executed by a computer using an interpreter. For example, an embodiment of the invention may be implemented using Java, C++, or other object-oriented programming language and development tools. Additional examples of computer code include, but are not limited to, control signals, encrypted code, and compressed code.

While certain embodiments have been shown and described above, it will be understood by those skilled in the art that various changes in form and details may be made. For example, variations in illumination techniques are possible and can allow an improvement to the modulo $\lambda/2$ periodicity of the intensity data. In addition, the various embodiments described in the Betzig references can be combined with the various embodiments described herein. For example, in one embodiment, top/bottom TIRF illumination can allow for measurements of a sample having a thickness up to one wavelength, $\lambda$. In alternative embodiments, coherent re-phasing of short pulses can form an illumination plane. In yet other embodiments, side illumination to form a Gaussian waist at the sample at various heights in the z-coordinate can further extend the range in the z-coordinate direction without resorting to physical sectioning. Thus, it should be understood that the systems described herein can include various combinations and/or sub-combinations of the components and/or features of the different embodiments described.

What is claimed is:

1. A method comprising:
    interfering optical energy emitted from a fiducial optical emitter in at least two directions to produce N fiducial output beams along N legs, where N is greater than or equal to 2;
    sequentially moving the fiducial optical emitter in a plurality of predetermined positions along a z axis;
    acquiring images based on each of the N fiducial output beams as the fiducial optical emitter is moved along the plurality of predetermined positions along the z axis to form an image frame sequence for each of the N fiducial output beams;
    determining, at each of the N legs and from the plurality of image frame sequences, at least one characteristic associated with each predetermined position of the fiducial optical emitter along the z axis; and
    storing the at least one characteristic and the predetermined positions of the fiducial optical emitter along the z axis.

2. The method of claim 1, wherein N is greater than or equal to 3.

3. The method of claim 1, wherein sequentially moving the fiducial optical emitter in the plurality of predetermined positioned along the z axis comprises incrementing a position of the fiducial optical emitter along the z axis.

4. The method of claim 1, wherein the fiducial optical emitter includes a plurality of fiducials, and the method further comprises transforming the images to produce transformed images that align the fiducials in the image in the x,y plane.

5. The method of claim 4, further comprising summing the acquired images at each of the N legs for each position in the z axis into summed image frames.

6. The method of claim 5, further comprising fitting the summed image frames to a predetermined distribution to determine a center of the fiducial optical emitter in the x,y plane.

7. The method of claim 6, further comprising:
fitting the transformed image frames to a predetermined distribution; and
measuring an amplitude of the emission distribution in each image frame at the determined center of the fiducial optical emitter in the x,y plane.

8. The method of claim 7, further comprising normalizing the amplitudes of the emission distribution, wherein storing the at least one characteristic and the predetermined positions of the fiducial optical emitter comprises recording the normalized amplitudes and associated position along the z axis.

9. The method of claim 1, wherein each acquired image in an image frame sequence is based on optical energy intensities in the x,y plane relating to the emission distribution of the fiducial optical emitter.

10. The method of claim 9, further comprising fitting the emission distributions of the fiducial optical emitter to a predetermined distribution to localize the emission distribution in the x,y plane.

11. The method of claim 1, further comprising correcting the images for drift using the fiducial optical emitter included in the images.

12. The method of claim 1, wherein the fiducial optical emitter includes a plurality of fiducials, and each fiducial is separable and identifiable as a sub-diffractive sized point source.

13. The method of claim 1, wherein the determined at least one characteristic associated with each predetermined position of the fiducial optical emitter along the z axis at one of the N legs includes a normalized peak optical energy intensity amplitude of the acquired image at that N leg.

14. The method of claim 1, wherein the determined at least one characteristic associated with each predetermined position of the fiducial optical emitter along the z axis at one of the N legs includes one or more of: a gain of the acquired image in the N leg, an interference correction factor in the N leg, and a phase shift in the N leg.

15. The method of claim 1, further comprising identifying a position of an optical emitter along the z axis based on the determined at least one characteristic associated with each predetermined position of the fiducial optical emitter along the z axis.

16. A method comprising:
interfering optical energy emitted from an optical emitter in at least two directions to produce N output beams along N legs, where N is greater than or equal to 2;
detecting N images based on the N output beams, each image being based on an output beam from the N output beams;
determining, at each of the N legs, at least one characteristic associated with a position of an optical emitter along a z axis based on the N images; and
correlating the at least one characteristic with a plurality of characteristics associated with a plurality of predetermined positions of a fiducial optical emitter along the z axis to identify the position of the optical emitter along the z axis.

17. The method of claim 16, further comprising:
identifying a position of the optical emitter in an x,y plane based on the detected N images.

18. The method of claim 17, further comprising:
interfering optical energy emitted from the fiducial optical emitter in at least two directions to produce N fiducial output beams along N legs;
sequentially moving the fiducial optical emitter along the plurality of predetermined positions along the z axis; and
acquiring images along each of the N legs based on each of the N fiducial output beams as the fiducial optical emitter is moved along the plurality of predetermined positions along the z axis to form an image frame sequence for each of the N fiducial output beams;
wherein the plurality of characteristics associated with the plurality of predetermined positions of the fiducial optical emitter are determined at each of the N legs and from the formed image frame sequence for each of the N fiducial output beams.

19. The method of claim 18, wherein the plurality of characteristics associated with the plurality of predetermined positions of the fiducial optical emitter along the z axis include a normalized peak optical energy intensity amplitude of the acquired image at that N leg.

20. The method of claim 18, wherein the plurality of characteristics associated with the plurality of predetermined positions of the fiducial optical emitter along the z axis includes one or more of: a gain of the acquired image in the N leg, an interference correction factor in the N leg, and a phase shift in the N leg.

21. The method of claim 16, wherein N is greater than or equal to 3.

22. The method of claim 16, wherein correlating the determined at least one characteristic with the plurality of characteristics comprises determining a minimum chi-square difference between the determined characteristic associated with the position of the optical emitter along the z axis and each characteristic associated with the predetermined positions of the fiducial optical emitter.

* * * * *